US012788642B2

(12) United States Patent
Stanley et al.

(10) Patent No.: US 12,788,642 B2
(45) Date of Patent: Nov. 10, 2026

(54) DURABLE ABSORBENT PANT

(71) Applicant: The Procter & Gamble Company, Cincinnati, OH (US)

(72) Inventors: Scott Kendyl Stanley, Mason, OH (US); Noel Leon Gauthier, Cincinnati, OH (US); Jesus Velazquez, West Chester, OH (US); Brian Kenneth Burgdorf, Cincinnati, OH (US); C. Michelle Dunaway, West Chester, OH (US); Jessica Wetzel, Cincinnati, OH (US); Andrew Paul Rapach, Fairfield, OH (US); Travis Kyle Hodgdon, Cincinnati, OH (US); Jessica Frances Hemmer, Cincinnati, OH (US); John Hart Kelly, Houston, TX (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 471 days.

(21) Appl. No.: 18/338,501

(22) Filed: Jun. 21, 2023

(65) Prior Publication Data

US 2024/0000622 A1 Jan. 4, 2024

Related U.S. Application Data

(60) Provisional application No. 63/356,691, filed on Jun. 29, 2022.

(51) Int. Cl.
*A61F 13/49* (2006.01)
*A61F 13/56* (2006.01)

(52) U.S. Cl.
CPC ...... *A61F 13/49003* (2013.01); *A61F 13/565* (2013.01)

(58) Field of Classification Search
CPC .............. A61F 13/49003; A61F 13/565; A61F 13/471; A61F 13/49004; A61F 13/49006; A61F 13/496; A61F 13/505; A61F 13/15268; A61F 2013/15276
See application file for complete search history.

(56) References Cited

U.S. PATENT DOCUMENTS

| | | | |
|---|---|---|---|
| 2,705,957 | A | 4/1955 | Virginia |
| 3,909,851 | A | 10/1975 | Garrou et al. |
| 4,355,425 | A | 10/1982 | Jones et al. |
| 5,085,653 | A | 2/1992 | Levy |
| 5,248,309 | A | 9/1993 | Serbiak |

(Continued)

FOREIGN PATENT DOCUMENTS

| | | | |
|---|---|---|---|
| CA | 2255465 | A1 | 6/2000 |
| CA | 2827795 | A1 | 11/2013 |

(Continued)

OTHER PUBLICATIONS

All Office Actions; U.S. Appl. No. 18/645,742, filed Apr. 25, 2024.

(Continued)

*Primary Examiner* — Susan S Su
(74) *Attorney, Agent, or Firm* — Sarah M. DeCristofaro

(57) ABSTRACT

This invention relates to features of durable absorbent pants (for example, underwear briefs) to be worn for containing and absorbing bodily discharges, wherein the pants include an integrated absorbent panel.

8 Claims, 11 Drawing Sheets

(56) References Cited

U.S. PATENT DOCUMENTS

| | | | | |
|---|---|---|---|---|
| 5,562,648 | A | 10/1996 | Peterson | |
| 5,851,204 | A | 12/1998 | Mizutani | |
| 6,258,455 | B1 | 7/2001 | Clarke | |
| 6,287,286 | B1 | 9/2001 | Akin et al. | |
| 6,393,621 | B1 | 5/2002 | Redwine et al. | |
| 6,884,494 | B1 | 4/2005 | Curro | |
| 7,118,639 | B2 | 10/2006 | Delucia et al. | |
| 7,322,966 | B1 | 1/2008 | Deerin | |
| 7,458,961 | B2 | 12/2008 | Carstens | |
| 7,462,173 | B2 | 12/2008 | Carstens | |
| 7,846,145 | B2 | 12/2010 | Carstens | |
| 8,099,794 | B2 | 1/2012 | Carstens | |
| 8,117,675 | B2 | 2/2012 | Strange et al. | |
| 8,262,638 | B2 | 9/2012 | Carstens | |
| 8,348,918 | B2 | 1/2013 | Carstens | |
| 8,454,570 | B2 | 6/2013 | Carstens | |
| 8,578,518 | B1 * | 11/2013 | Pflug | A41B 9/06 2/117 |
| 8,679,085 | B2 | 3/2014 | Ronstroem | |
| 8,998,870 | B2 | 4/2015 | Roe | |
| 9,980,861 | B2 | 5/2018 | Deerin | |
| 10,441,480 | B2 | 10/2019 | Griffiths | |
| 10,966,873 | B2 | 4/2021 | Schneider | |
| 11,154,431 | B1 | 10/2021 | Yip et al. | |
| 11,207,225 | B2 | 12/2021 | Kajanthan | |
| 11,395,774 | B2 | 7/2022 | Skinner | |
| 12,295,438 | B2 * | 5/2025 | Deshaies | A41D 31/125 |
| 2002/0004349 | A1 | 1/2002 | Tsujiyama et al. | |
| 2002/0016580 | A1 | 2/2002 | Wada | |
| 2003/0097109 | A1 | 5/2003 | Bruce | |
| 2005/0120466 | A1 | 6/2005 | Coenen et al. | |
| 2005/0142331 | A1 | 6/2005 | Anderson | |
| 2005/0229293 | A1 | 10/2005 | Miller | |
| 2006/0070163 | A1 | 4/2006 | Beck | |
| 2006/0264869 | A1 | 11/2006 | Carstens | |
| 2006/0264883 | A1 | 11/2006 | Carstens | |
| 2006/0264884 | A1 | 11/2006 | Carstens | |
| 2007/0012519 | A1 | 1/2007 | Angielski | |
| 2007/0106354 | A1 | 5/2007 | Carstens | |
| 2007/0245449 | A1 | 10/2007 | Ehmsen et al. | |
| 2008/0147031 | A1 | 6/2008 | Long et al. | |
| 2010/0249736 | A1 | 9/2010 | Png et al. | |
| 2011/0172621 | A1 | 7/2011 | Lee | |
| 2013/0226120 | A1 | 8/2013 | Van | |
| 2014/0018763 | A1 | 1/2014 | Evenson et al. | |
| 2014/0039432 | A1 | 2/2014 | Dunbar et al. | |
| 2014/0257228 | A1 | 9/2014 | Wang et al. | |
| 2014/0257229 | A1 | 9/2014 | Wang et al. | |
| 2016/0089276 | A1 | 3/2016 | Griffiths | |
| 2016/0100997 | A1 | 4/2016 | Seitz | |
| 2016/0166447 | A1 | 6/2016 | Toro | |
| 2016/0184146 | A1 | 6/2016 | Tulk | |
| 2018/0014983 | A1 * | 1/2018 | Jayasuriya | A61L 15/26 |
| 2020/0000155 | A1 | 1/2020 | Etienne | |
| 2021/0030605 | A1 * | 2/2021 | Kajanthan | A61F 13/49006 |
| 2021/0100698 | A1 | 4/2021 | Langdon et al. | |
| 2021/0290447 | A1 | 9/2021 | Sepello et al. | |
| 2022/0354710 | A1 | 11/2022 | Sepello et al. | |
| 2023/0109095 | A1 * | 4/2023 | Yip | A61F 13/4942 604/385.01 |
| 2023/0129586 | A1 * | 4/2023 | Greco | A41D 7/00 604/383 |
| 2023/0157375 | A1 | 5/2023 | Seitz | |
| 2024/0065901 | A1 | 2/2024 | Stanley | |

FOREIGN PATENT DOCUMENTS

| | | | |
|---|---|---|---|
| CN | 101926709 | A | 12/2010 |
| EP | 0811362 | A1 | 12/1997 |
| EP | 1166738 | A2 | 1/2002 |
| EP | 1370161 | B1 | 12/2003 |
| EP | 2412353 | A2 | 2/2012 |
| EP | 2968030 | B1 | 4/2018 |
| JP | 4266604 | B2 | 2/2009 |
| KR | 100694187 | B1 | 3/2007 |
| WO | 2004004619 | A1 | 1/2004 |
| WO | 2013148749 | A1 | 10/2013 |
| WO | 2013186577 | A1 | 12/2013 |
| WO | 2015156686 | A2 | 10/2015 |
| WO | 2021155397 | A1 | 8/2021 |
| WO | 2022235734 | A1 | 11/2022 |

OTHER PUBLICATIONS

Anonymous, "Femtis—Perioden Panties—Periodenslip Ella", XP093016146, Retrieved from the Internet: URL: https://web.archive.org/web/20210726170425/https://www.femtis.de/periodenslips/perioden-slip-ella-rot.html [retrieved on Jan. 20, 2023], Jul. 26, 2021, 9 pages.

Anonymous, "Inkontinenzslip: hydas.de", XP093016138, Retrieved from the Internet: URL: https://web.archive.org/web/20210412055014/https://www.hydas.de/inkontinenzslip [retrieved on Jan. 20, 2023], Apr. 12, 2021, 57 pages.

Anonymous, "Periodenpantys 2er-Pack Spitze schwarz—Secret Care", XP093016049, Retrieved from the Internet: URL: https://web.archive.org/web/20210415173928/https://www.schiesser.com/damenbekleidung-unterwaesche-slips-pants-periodenpantys-2er-pack-spitze-schwarz-secret-care.html [retrieved on Jan. 20, 2023], Apr. 15, 2021, 19 pages.

U.S. Appl. No. 18/645,742, filed Apr. 25, 2024, to Jill Marlene Orr et al.

WO Search Report and Written Opinion for PCT/US2023/068764 dated Oct. 19, 2023, 11 pages.

All Office Actions; U.S. Appl. No. 18/447,363, filed Aug. 10, 2023.

U.S. Appl. No. 18/447,363, filed Aug. 10, 2023, to Ashley Basius et al.

* cited by examiner

DURABLE ABSORBENT PANT

FIELD OF THE INVENTION

This invention relates to features of durable absorbent pants (for example, underwear briefs) to be worn for containing and absorbing discharges resulting from urinary incontinence, where the pants comprise an absorbent panel that is smoothly integrated into the pants.

BACKGROUND

In recent years populations in many developed countries have shifted toward middle-aged and older demographic groups. These demographic groups represent markets with relatively increased demands for products addressed to concerns associated with aging.

One such concern is adult urinary incontinence. Urinary incontinence can result from or be exacerbated by a variety of health conditions or simply aging.

Disposable absorbent pants for adults experiencing urinary incontinence have been marketed for a number of years. These products have traditionally exhibited varying degrees of similarities in appearance, feel and bulkiness to disposable diapers or disposable children's training pants. Finding these similarities undesirable, many active people experiencing only mild to moderate incontinence have preferred not to use these products, opting to use durable/washable absorbent underwear, or durable ordinary underwear in combination with a disposable absorbent pad held in place by/within the underwear.

A problem presented in designing a system to be used to contain and absorb unintended small discharges of urine by a man lies in the male anatomy and the tendency of urine to exit the body when the penis is in a variety of positions. Depending upon the man's body and penis position during an unintended discharge, urine flow can find its way through gaps between the skin and containment features of the selected containment/absorbent system (e.g. underwear leg bands, cuffs and other containment features of absorbent underwear and/or pad), and thereby, escape capture by the absorbent portions of the system and soil surrounding portions of underwear, outer clothing, bedclothes, etc. Also, the flow rate and amount of the urine in the male anatomy is quite different from the flow rate in the female anatomy, thus existing female incontinence products are not designed to work with the male anatomy.

Currently available durable absorbent pants that incorporate absorbent structures do not sufficiently maintain contact with the male anatomy and/or do not provide an optimal in-wear experience, e.g., durable absorbent pants that are comfortable and discrete under clothing. There is a need for durable absorbent pants for men that comprise an absorbent front panel that is smoothly integrated into the pants, making the pants more comfortable to wear and more discreet under clothing.

DEFINITIONS

Figure 1:
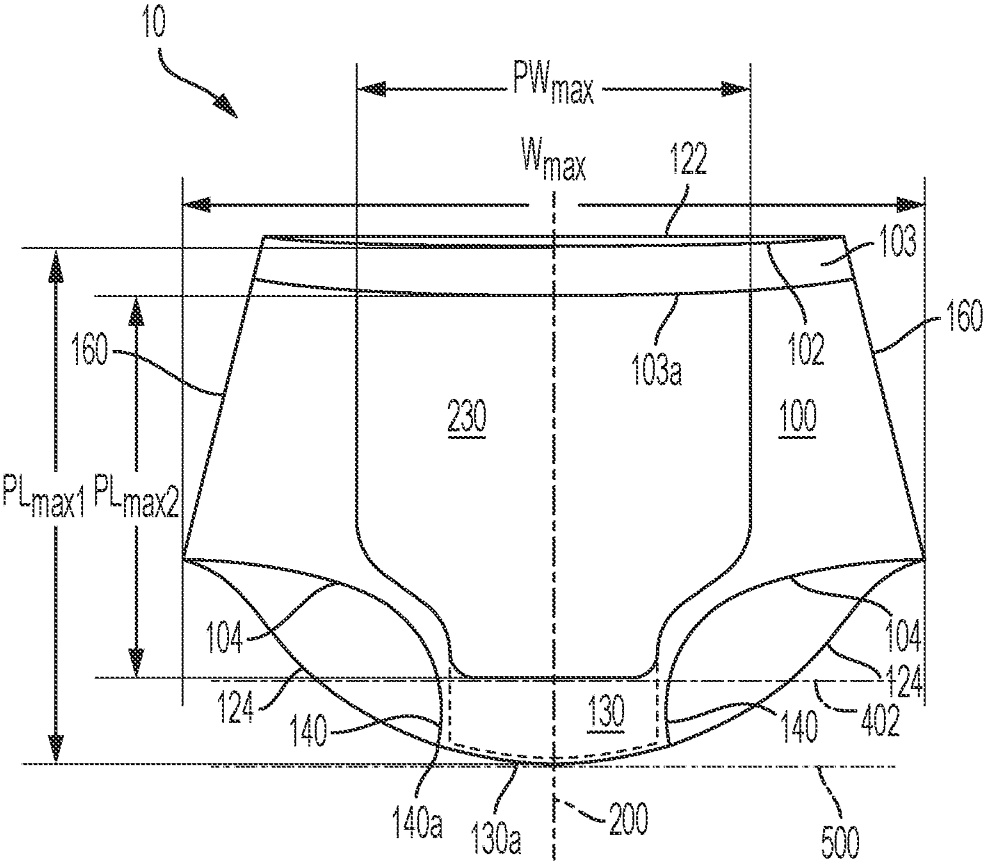
FIG. 1 is a simplified depiction of an example of a brief pant, as it would appear laid out flat on a horizontal planar surface, front waist portion facing up.

With respect to a wearable garment such as a pant, "durable" means made predominately of cloth or textile material that is knitted and/or woven from natural, semi-synthetic or synthetic fiber, thread or yarn, and which may be normally laundered or hand-washed and dried for reuse/re-wear a plurality of times without substantial loss of original shape, structure or useful mechanical attributes.

With respect to a pant in an opened configuration, laid out flat on a horizontal planar surface, "longitudinal" refers to a direction generally perpendicular to a line tangent each of the left and right leg opening edges where they are closest the front waist edge. With respect to a pant in an assembled configuration, laid out flat on a horizontal planar surface, front waist portion facing up, "longitudinal" refers to a direction generally perpendicular to a line tangent each of the left and right leg opening edges where they are closest the front waist edge. "Length" refers to a dimension measured along the longitudinal direction.

With respect to a pant in an opened configuration, laid out flat on a horizontal planar surface, "lateral" refers to a direction generally parallel to a line tangent each of the left and right leg opening edges where they are closest the front waist edge. With respect to a pant in an assembled configuration, laid out flat on a horizontal planar surface, front waist portion facing up, "lateral" refers to a direction generally parallel to a line tangent each of the left and right leg opening edges where they are closest the front waist edge. "Width" refers to a dimension measured along the lateral direction.

With respect to a pant in an opened configuration, laid out flat on a horizontal planar surface, the "z-direction" is the direction orthogonal to the longitudinal and lateral directions, i.e., the vertical direction relative the horizontal planar surface.

With respect to respective layer components in an absorbent front panel of a pant in an opened configuration, laid out flat on a horizontal planar surface, wearer-facing surfaces facing up, as between first and second layer components in the absorbent panel, the terms "above," "superadjacent," "below," "subjacent" and/or "beneath" describe the components' disposition along the z-direction relative each other. Thus, for example, referring to FIG. 5A, a wearer-facing layer 231*a* is disposed "above" an absorbent layer 231*b*, and conversely, the liquid impervious barrier layer 231*c* is disposed "below" the wearer-facing layer 231*a* and the absorbent layer 231*b*. "Superadjacent" and "subjacent" with respect to two-layer components, mean further that the two-layer components are disposed in direct surface-to-surface contact with each other.

A yarn, thread, fiber, filament, web, film or fabric material, or a laminate or composite of any of these, is considered to be "elastic" or "elastomeric" for purposes herein if, when a tensile force no greater than 50 gf/mm (gf per mm of sample width, where width is measured perpendicular to the stretch direction) is applied to the subject material along a stretch direction, the material may be extended along the direction to an elongated dimension of at least 130% of its original relaxed dimension (i.e., can extend at least 30%), without rupture or breakage which substantially damages the subject material; and when the force is removed from the subject material, the material retracts along the stretch direction to recover at least 40% of such elongation. To illustrate, if a section of fabric having an original relaxed length of 100 mm and a width of 40 mm can be elongated by tensile force of 2000 gf (50 gf/mm) in a direction along its length to 130 mm length without substantial damage and will retract upon removal of the force to a length no greater than 118 mm (130 mm−118 mm=12 mm=40% of 30 mm), it is "elastic" as defined herein. "Elongation," used herein to quantify and express an amount of strain imparted to an elastic material in a stretch direction, means: {[(strained length of the strand)−(length of the strand before straining)]/(length of the strand before straining)}, ×100%.

With respect to two opposing surfaces of a layer component of a pant, or combination of layer components, "wearer-facing" refers to the surface that faces the wearer's skin when the pant is worn normally; and "outward-facing" refers to the surface that faces away from the wearer's skin. With respect to two distinct layered components of a pant, the "wearer-facing" component is the component that is disposed closest the wearer's skin when the pant is worn normally; and the "outward-facing" component is the component that is disposed farthest from the wearer's skin when the pant is worn normally.

For purposes herein, "pant" includes any garment adapted for wear about the human lower torso, including a front waist portion and a rear waist portion that join about the wearer's hips and beneath the wearer's crotch, to form a garment having a waist opening and a pair of leg openings. Herein, the term "pant" encompasses (but is not limited to) a garment defined herein as a "brief pant"; a garment defined herein as a "legged pant", and any other garment (e.g., boxer, boxer brief, bikini) whether adapted for use as underwear or outerwear, having such features.

For purposes herein, unless otherwise specified, with respect to the proportionate content of a component material in a combination or structure, "predominate" means the component constitutes the majority of the weight of the combination or structure.

Figure 3:
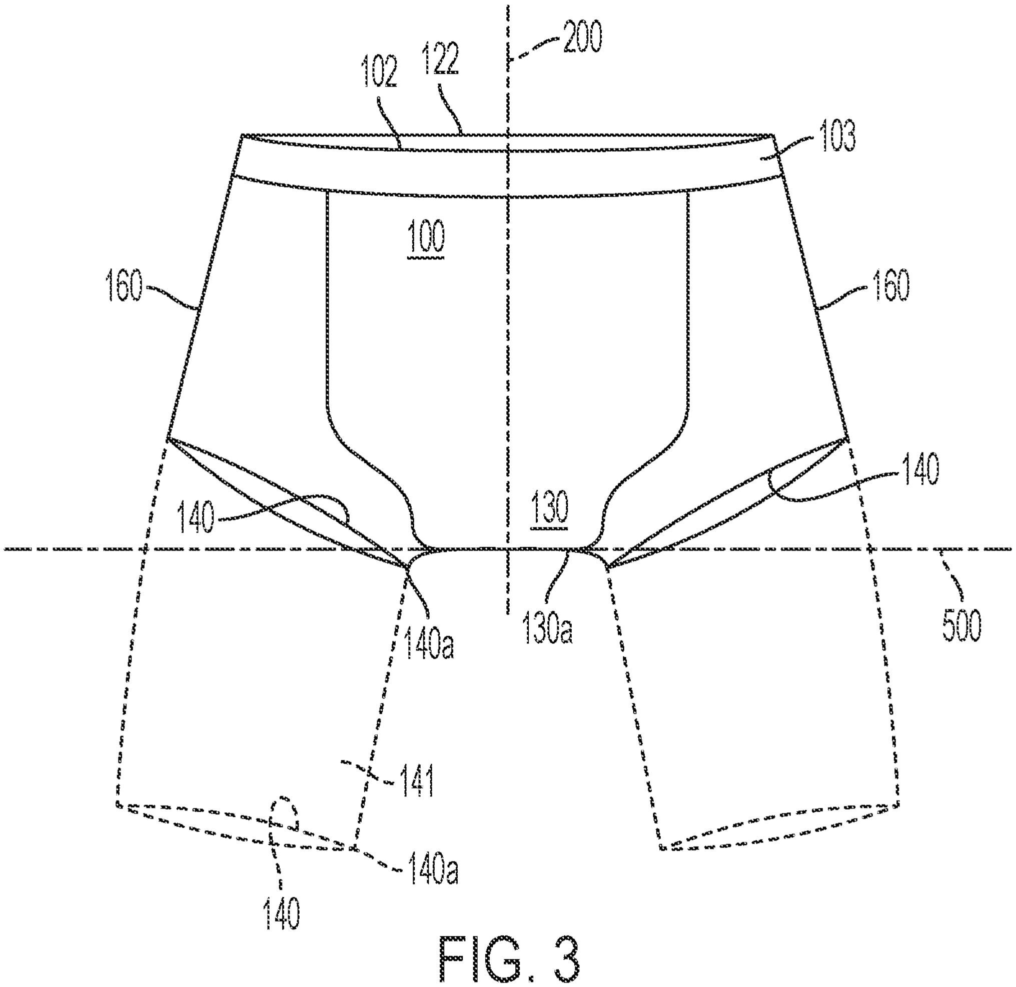
FIG. 3 is a simplified depiction of an example of a shorts pant (or legged pant), as it would appear laid out flat on a horizontal planar surface, front waist portion facing up.

For purposes herein, a "brief pant" is distinguished from a "legged pant" by the configuration of the inside leg edges, resulting from the manner in which the component materials are shaped, sized, proportioned and seamed or otherwise affixed together. FIG. 1 depicts an example of a brief pant and FIG. 3 depicts an example of a legged pant in alternative forms. When the garment in its assembled condition is laid out flat on a horizontal planar surface, front waist portion facing up with the front waist edge 102 lined up with or coincident with the rear waist edge 122, and a lateral crotch tangent line 500 is drawn perpendicularly to longitudinal axis 200 and tangent to the point at which the crotch portion lower profile 130*a* intersects the longitudinal axis 200, for a brief pant, the lowermost points 140*a* along the inside leg opening edges 140 are disposed along or above the crotch tangent line 500 (i.e., toward the front waist edge 102) (see FIG. 1); and for a legged pant, the lowermost points 140*a*, 150*a* along the inside leg opening edges 140, 150 are disposed below the crotch tangent line 500 (i.e., away from the front waist edge 102) (see FIG. 3). As reflected in FIG. 3, for purposes herein, a legged pant may have leg portions 141 of any length, wherein the lowermost points 140*a*, 150*a* of inside leg opening edges 140, 150 are disposed below the crotch tangent line 500. Underwear shorts pants such as "shorts" or "trunk" styles will generally have shorter leg portions as suggested in the solid-line portions of FIG. 3, while other legged pants may have leg portions of varying lengths, as suggested by the dashed-line portions of FIG. 3.

As used herein, "perimeter seal" refers to an element that joins one or more layers of an absorbent panel along the entire perimeter of the absorbent panel, thus sealing the perimeter of the of the absorbent panel. Perimeter seals as described herein may inhibit leakage of fluids captured in the absorbent panel outside the perimeter of the absorbent panel and onto the front waist portion or crotch portion of the pant.

DESCRIPTION OF EMBODIMENTS

As noted above, a problem presented in designing an absorbent system to be used to contain and absorb unintended (incontinent) small discharges of urine and/or other bodily fluids by a man is the wide variability of penis orientations during an unintended discharge. If features of a chosen containment/absorbency system do not reliably hold absorbent materials against the wearer's skin to intercept flow from a variety of penis orientations, leakage can result. However, it is also preferable that the features of a chosen containment/absorbency system, particularly the absorbent front panel, do not wrap around the male genitalia, as this may cause discomfort during wear.

Figure 7A:
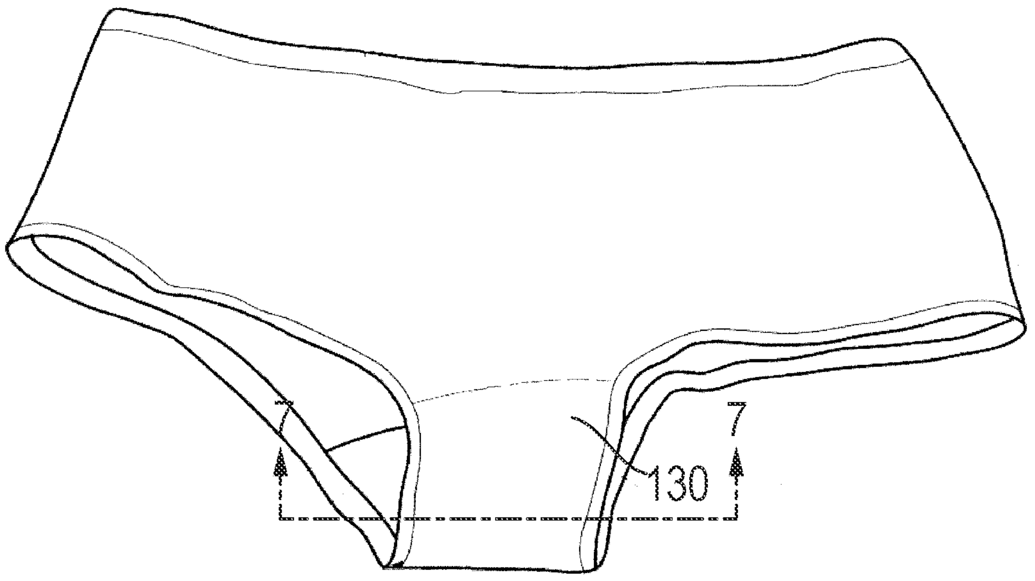
FIG. 7A is a simplified depiction of an example of a brief pant for women, front waist portion facing up.
Figure 7B:
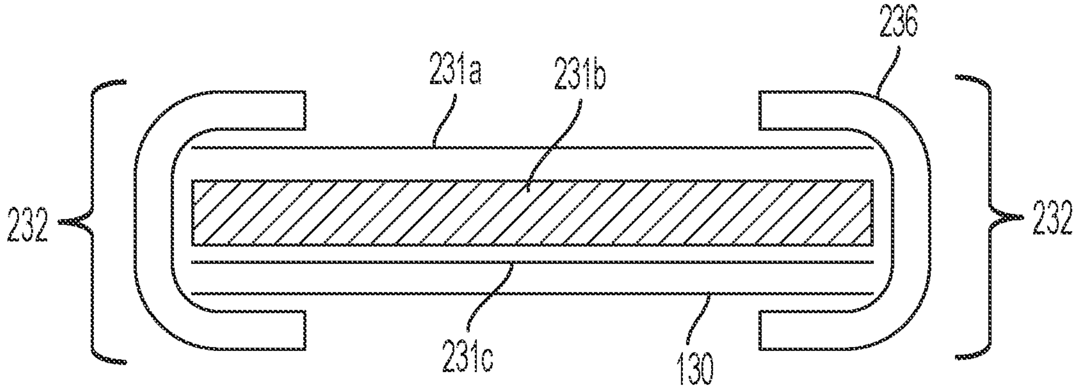
FIG. 7B is a magnified schematic lateral cross section of an example of a brief pant as depicted in FIG. 7A, taken along line 7-7 in the crotch portion of the pant.
Figure 8A:
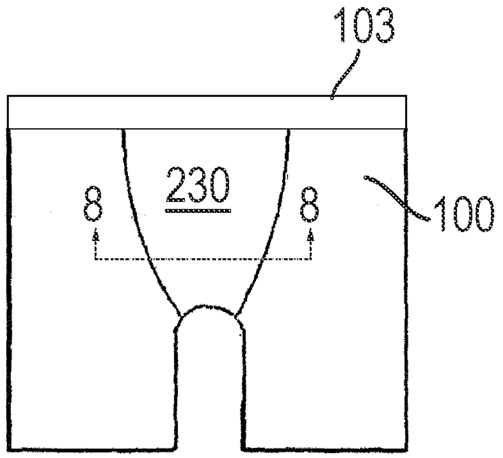
FIG. 8A is a simplified depiction of an example of a brief pant for men, front waist portion facing up.
Figure 8B:
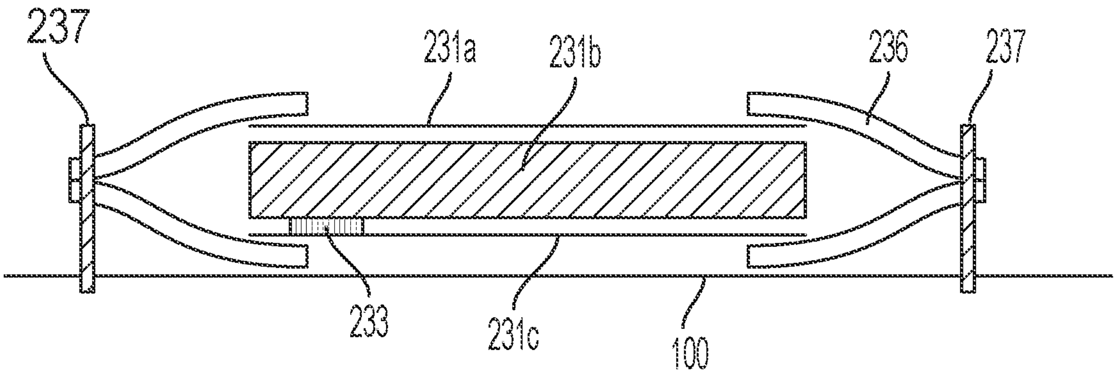
FIG. 8B is a magnified schematic lateral cross section of an example of a brief pant as depicted in FIG. 8A, taken along line 8-8.
Figure 9A:
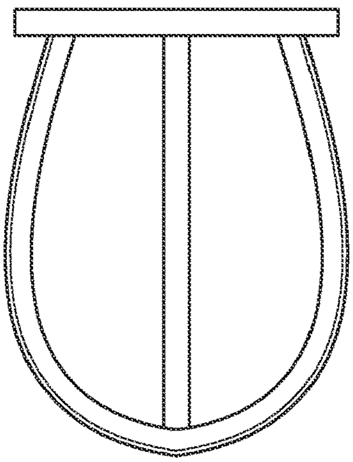
FIG. 9A is a plan view of an example of an absorbent front panel, including a wearer-facing layer, an absorbent layer, a liquid impermeable barrier layer, and sealing tape(s), laid out on a horizontal surface, outward-facing surface facing the viewer.
Figure 9B:
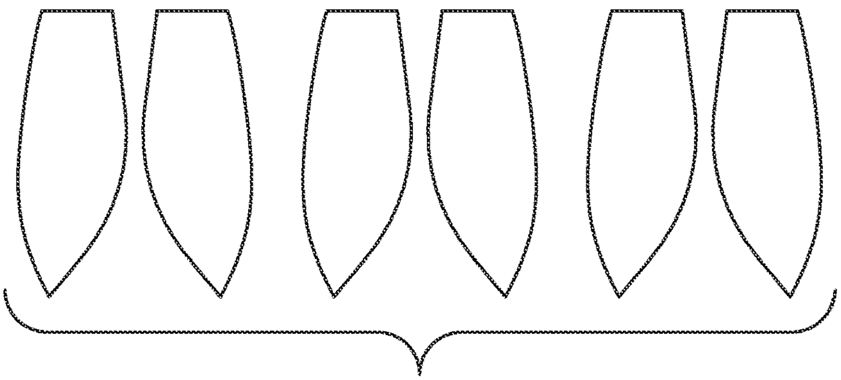
FIG. 9B is a simplified depiction of cutting shapes for an example of an absorbent front panel as depicted in FIG. 9A, where each shape includes a wearer-facing layer, an absorbent layer, and a liquid impermeable barrier layer.
Figure 9C:
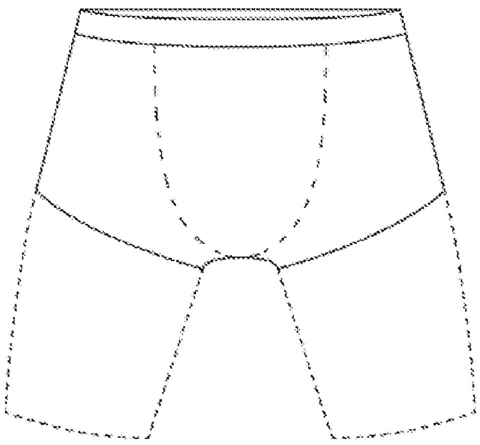
FIG. 9C is a simplified depiction of an example of a shorts pant (or legged pant) incorporating the absorbent front panel of FIG. 9A, as it would appear laid out flat on a horizontal planar surface, front waist portion facing up.

It is believed, however, that a durable adult absorbent brief pant (i.e., a pant with a front panel including an absorbent structure and a liquid impermeable barrier layer to the outside thereof), that is comfortable to wear and discrete under clothing, while also reliably protecting against leakage through a variety of body movements and penis positions (and over a reasonable duration of wear/use) has not been marketed to date. In currently marketed absorbent pants, the absorbent front panel is not smoothly integrated into the pants, making the pants less comfortable to wear and less discreet under clothing. Some currently marketed absorbent pants comprise perimeter seals 232 that include the absorbent layer 231*b* of the absorbent panel and/or every layer of the absorbent panel 231*b*, as shown in FIG. 7B, which is a magnified schematic lateral cross section of the crotch portion 130 of a pant designed for women, as depicted in FIG. 7A, taken along line 7-7. Some currently marketed absorbent pants designed for men also comprise perimeter seals that include the absorbent layer of the absorbent panel and/or every layer of the absorbent panel, as shown in FIG. 8B, which is a magnified schematic lateral cross section of the absorbent front panel 230 of a pant designed for men, as depicted in FIG. 8*a*, taken along line 8-8. As shown in FIG. 8B, in the absorbent panel 230, tape 236 joins the wearer-facing layer 231*a*, the absorbent layer 231*b*, and the liquid impermeable barrier layer 231*c*, and the absorbent layer 231*b* is also joined to the liquid impermeable barrier layer 231*c* with adhesive 233. The absorbent panel 230 is joined to the front waist portion 100 via a stitched seam 237.

Currently marketed pant products also do not effectively hold included absorbent structures against the body through various body movements, over a reasonable duration of wear/use and still remain flexible in bending (e.g., low handle). The human body has geometrically non-ruled contoured surfaces. Fabrics or web materials that do not exhibit an effective amount of elastic stretch capability along an effective direction will not effectively conform closely to (i.e., remain in contact with) the substantial majorities or entireties of these surfaces through ordinary body positions and movements. Increasing the amount of elastic stretch capability and reducing the handle imparted to the absorbent front panel increases the variety of body shapes and movements to which the absorbent front panel can conform in use. In connection therewith, reducing the longitudinal tensile modulus (longitudinal tensile force in the material resulting from longitudinal stretching) and handle tends also to increase body conformity and enhance comfort.

For underwear, some men prefer brief pants rather than legged pants, such as "shorts" or "trunk" styles, for ordinary daily wear. This is due to issues of comfort; unlike a legged, shorts-type pant, a brief pant ordinarily will not ride up and bunch about the legs from changes of body position, and thereby be a source of unwanted concentration of material bulk, tightness about the legs or other discomfort under outer clothing. Further, due to the manner in which their leg edges tend to cause the pant to fit through the crotch region of the body, brief pants having suitable elastic stretch characteristics may be preferred for maintaining a close fit about the male genital/urethra area, for purposes of protecting against leakage of unintended discharges of urine.

Figure 2:
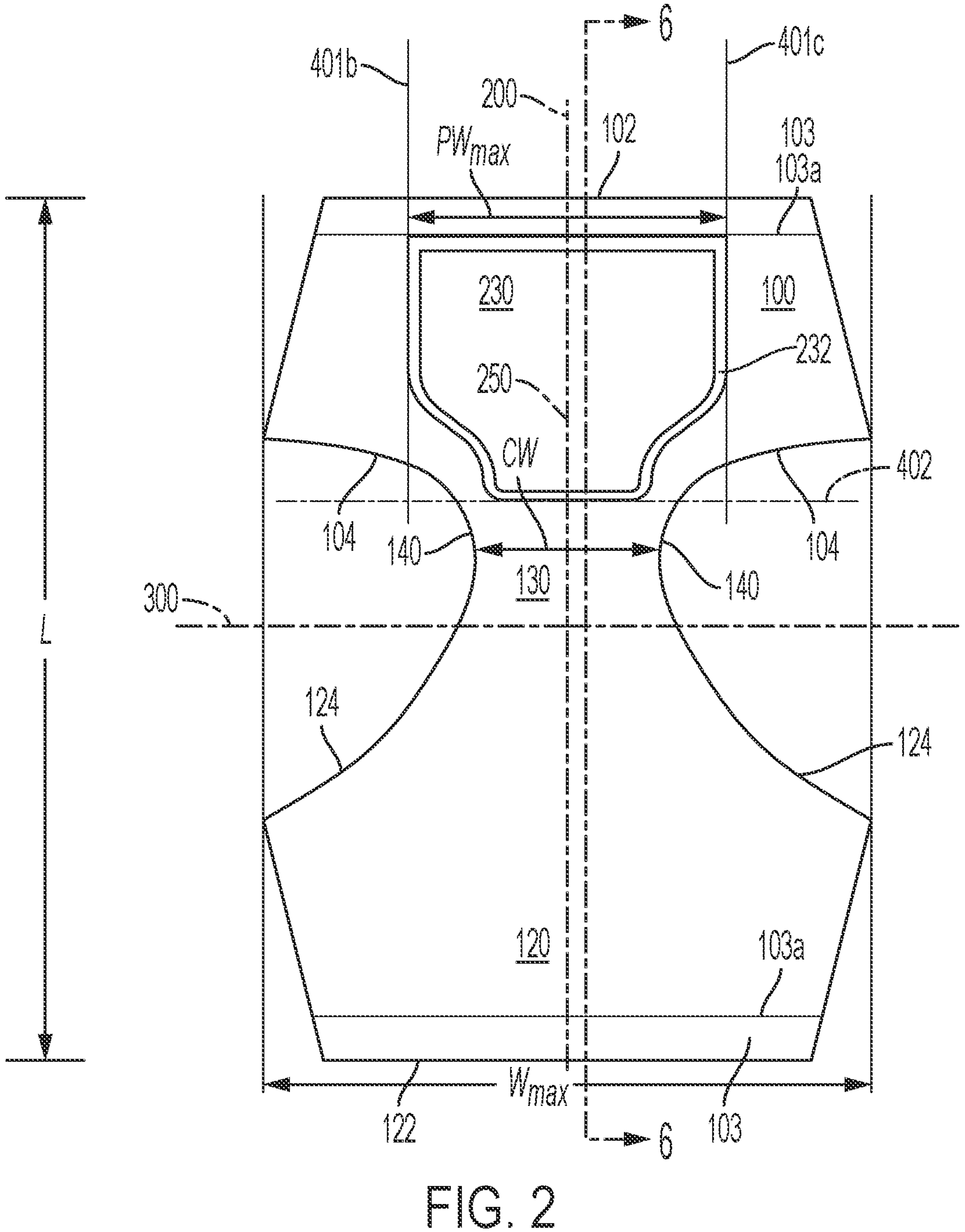
FIG. 2 is a depiction of the brief pant of FIG. 1, in an opened configuration where the front and rear waist portions have been separated at the hip portions or hip side seams, as it would appear laid out flat on a horizontal planar surface, wearer-facing surfaces facing up.

Referring to FIGS. 1 and 2 as illustrative but non-limiting examples, a pant 10 may include a longitudinal axis 200, a lateral axis 300 (which equally divides overall length L), a front waist portion 100, a rear waist portion 120, and a crotch portion 130 (which may include a separate element known as a crotch gusset) bridging the front and rear waist portions. Front waist portion 100 has a front waist edge 102 and left and right front leg opening edges 104. Rear waist portion 120 has a rear waist edge 122 and left and right rear leg opening edges 124. As shown in FIGS. 1, 2, 3, 6, and 7, pant 10 may include a waist band 103, such as an elastic waist band, for retention of the pant 10. Crotch portion 130 has left and right crotch leg opening edges 140 and bridges the front waist portion 100 and the rear waist portion 120. Front waist portion 100 may include, comprise, or consist of an absorbent panel 230 (also referred to herein as an absorbent front panel) that may include several layer components that will be described further below. For purposes herein, the "front waist portion 100" is a portion of a pant 10 identified as described herein, independently of specific components or structures. An "absorbent panel 230" or an "absorbent front panel 230" is a structural component that includes at least two distinct layers including an absorbent layer and a liquid impermeable barrier layer. An absorbent panel 230 has a "liquid impermeable barrier layer" if it exhibits z-Direction Leakage no greater than 0.1 ml of test fluid into a section of filter paper, in the Liquid Impermeability test described below. The pant 10 may include left and right hip side portions 160 joining the front waist portion 100 to the rear waist portion 120 and thereby forming a waist opening with a waist opening edge comprising the front waist edge 102 and the rear waist edge 122, and left and right leg openings, such that when the pant 10 is in an opened configuration, the front waist portion and rear waist portion are separated at the hip side portions.

The crotch portion 130 may extend laterally between left and right crotch leg opening edges 140, where the smallest width dimension CW is measured between the crotch leg opening edges 140. The crotch portion 130 may vary in length and the length of the crotch portion 130 may range from about 1% of the overall length L of the pant to about 65% of the overall length L of the pant, preferably from about 2% of the overall length L of the pant to about 45% of the overall length L of the pant, more preferably from about 5% of the overall length L of the pant to about 25% of the overall length L of the pant. The crotch portion 130 may be joined to the front waist portion 100 and the rear waist portion 120 by respective seams that may be present to join material(s) included in the crotch portion 130 and material(s) included in the front and rear waist portions 100, 120. The respective boundaries between the crotch portion 130 and the front and rear waist portions 100, 120, for purposes herein, may be independent of the location(s) of any seams that may be present to join material(s) included in the crotch portion 130 and material(s) included in the front and rear waist portions 100, 120. The pant may not have a crotch portion 130 and the front waist portion 100 may be joined directly to the rear waist portion 120, via a seam or otherwise.

Absorbent Panel

The absorbent panel may be durable, washable, and/or reversibly removable. The absorbent panel may be shaped and configured to conform to a non-ruled or non-planar surface. The elongation and stretch characteristics described below with respect to the absorbent panel would be applicable to the one or more layers of material in combination present in the absorbent front panel 230.

The absorbent panel may comprise a wearer-facing layer 231*a*, an absorbent layer 231*b* disposed to the outward-facing side of the wearer-facing layer 231*a*, and a liquid impermeable barrier layer 231*c* disposed to the outward-facing side of the absorbent layer 231*b*. The wearer-facing layer 231*a* may be a knitted fabric material. The absorbent layer 231*b* may optionally be joined 233 to the wearer-facing layer 231*a*, the liquid impermeable barrier layer 231*c*, or both, e.g., by adhesive. The absorbent panel may optionally comprise more than one absorbent layer, for example, two, three, or more absorbent layers. When the absorbent panel comprises multiple absorbent layers, the absorbent layers may be joined to each other, e.g., by an adhesive or stitched seam.

Alternatively, the absorbent panel may comprise an absorbent layer 231*b* and a liquid impermeable barrier layer 231*c* disposed to the outward-facing side of the absorbent layer 231*b*, where the absorbent layer 231*b* is the wearer-facing layer, as shown in FIG. 7A and FIG. 7B.

Figure 4A:
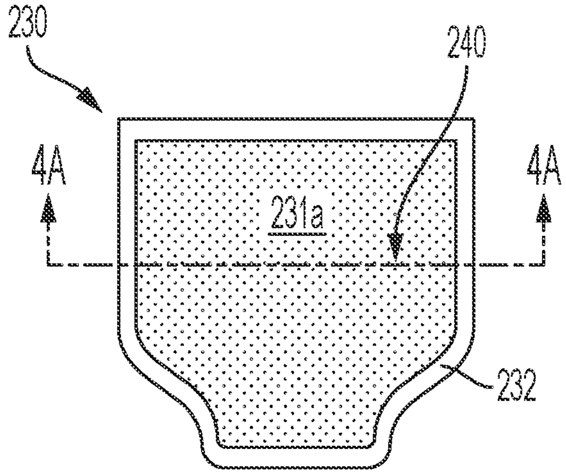
FIG. 4A is a plan view of an example of an absorbent front panel laid out on a horizontal surface, wearer-facing surface facing the viewer.
Figure 5A:
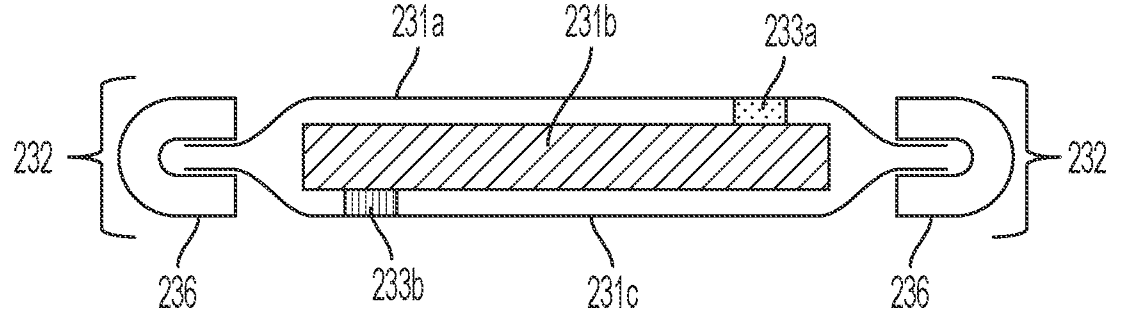
FIG. 5A-5C are schematic lateral cross sections of an example of an absorbent front panel as depicted in FIG. 4A, taken along line 4-4, showing different perimeter seals.
Figure 5B:
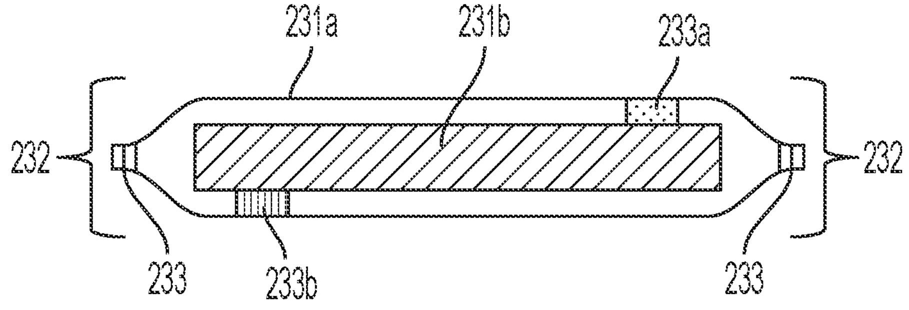
Figure 5C:
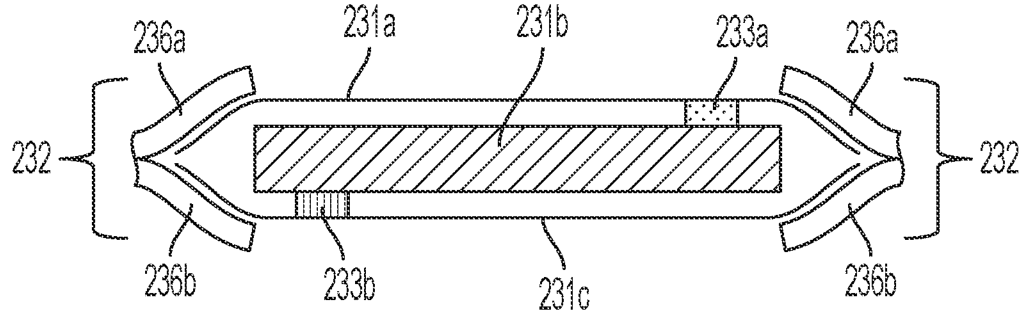

The wearer-facing layer 231*a* and the liquid impermeable barrier layer 231*c* may extend beyond the absorbent layer 231*b*, and the wearer-facing layer 231*a* may be joined directly to the liquid impermeable barrier layer 231*c*, by adhesive, tape, thermal bonding, or a combination thereof, preferably tape, to form a liquid impermeable seal 232 around a perimeter of the absorbent layer 231*b*, as shown in FIG. 4A. As shown in FIG. 5A, the wearer-facing layer 231*a* may be joined directly to the liquid impermeable barrier layer 231*c* to form a liquid impermeable seal 232 around the perimeter of the absorbent layer 231*b* by a C-folded tape 236. Alternatively, as shown in FIG. 5B, the wearer-facing layer 231*a* may be joined directly to the liquid impermeable barrier layer 231*c* by an adhesive 233 to form a liquid impermeable seal 232 around the perimeter of the absorbent layer 231*b*. Alternatively, as shown in FIG. 5C, the wearer-facing layer 231*a* may be joined directly to the liquid impermeable barrier layer 231*c* to form a liquid impermeable seal 232 around a perimeter of the absorbent layer 231*b* by a first tape 236*a* and a second tape 236*b*, the first tape 236*a* being joined to the wearer-facing layer 231*a* and the second tape 236*b* and the second tape 236*b* being joined to the liquid impermeable barrier layer 231*c* and the first tape 236*a*, preferably provided that the first tape 236*a* and the second tape 236*b* do not overlap the absorbent layer 231*b*. The tape, which is described in greater detail below, may have a width of about 3 mm to about 25 mm. The tape may be stretchable.

Materials respectively forming waist band 103, front waist portion 100, crotch portion 130, and/or rear waist portion 120 may be separate and distinct, and joined via any suitable attachment mechanism (not shown). Such an approach may provide the designer with greater flexibility in selection of the respective materials for the waist band, the front waist portion, the crotch portion, and the rear waist portion with respect to appearance, feel, weight, breathability, elongation, stretch characteristics and cost. Alternatively, material(s) forming waist band 103 may be continuous with material(s) forming the front waist portion 100, the rear waist portion 120, and/or the crotch portion 130. Material(s) forming the absorbent front panel 230 may be continuous with material(s) forming the front waist portion 100, the rear waist portion 120, and/or the crotch portion 130 and the front waist portion 100, the rear waist portion 120, and/or the crotch portion 130 may comprise a liquid impermeable layer (e.g., where there is overlap with the absorbent panel).

Or, alternatively, material(s) forming the absorbent front panel 230 may be substantially formed of one or more sections or layers of material that are distinct from material(s) substantially forming the front waist portion 100, the rear waist portion 120, and/or the crotch portion 130, and the absorbent front panel 230 may be joined to the front waist portion 100, the rear waist portion 120, and/or the crotch portion 130 by tape or a seam, for example. In illustrative but non-limiting examples reflected in FIGS. 6A-6D, waist band 103, front waist portion 100, and crotch portion 130 may be formed partially or entirely of a first single, continuous section of material, while the absorbent front panel 230 may be separate and distinct, and joined via any suitable attachment mechanism. In the examples shown in FIGS. 6A-6D, the layers of material 231*a*, 231*b*, 231*c* that form the absorbent front panel 230 are affixed to the wearer-facing side of the front waist portion 100 via, e.g., stitching/sewing, adhesive bonding, sew free, thermal bonding (fusing or welding), and/or other suitable attachment/joining mechanism (hereinafter, attachment mechanism).

The durable (and/or washable) absorbent pant disclosed herein may comprise an absorbent panel 230, a front waist portion 100 with a front waist edge 102, an optional waist band 103, and left and right front leg opening edges 104, the front waist portion 100 comprising the absorbent panel 230, a rear waist portion 120 with a rear waist edge 122 and left and right rear leg opening edges 124, a crotch portion 130 that bridges the front waist portion 100 and the rear waist portion 120, and left and right hip side portions 160 that join the front waist portion to the rear waist portion to form a waist opening with a waist opening edge comprising the front waist edge 102 and the rear waist edge 122, and left and right leg openings. The absorbent panel 230 may extend longitudinally from near the front waist edge 102 or the edge 103*a* of the optional waist band 103 of the pant to a minimum rear extent 402 and laterally from a left lateral edge 401*b* to a right lateral edge 401*c*. Preferably, each of the front waist portion 100, rear waist portion 120, and crotch portion 130 comprises a knitted material. The absorbent panel may be irreversibly joined to the pant, preferably to the front waist portion of the pant, using adhesive, tape, stitching, thermal bonding, ultrasonic welding, or a combination thereof, preferably tape. The absorbent panel 230 may be reversibly joined to the pant using, for example, Velcro, adhesive, or a combination thereof.

Figure 6A:
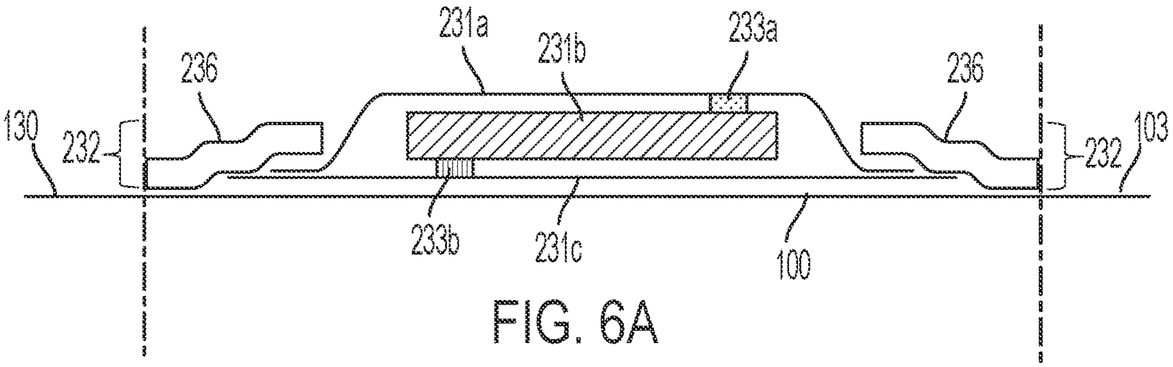
FIG. 6A-6D are schematic vertical cross sections of an example of a brief pant as depicted in FIG. 2, taken along line 6-6, showing different perimeter seals.

The pant, preferably the front waist portion 100 of the pant, may comprise an absorbent panel comprising a wearer-facing layer 231*a*, an absorbent layer 231*b* disposed to the outward-facing side of the wearer-facing layer 231*a*, and a liquid impermeable barrier layer 231*c* disposed to the outward-facing side of the absorbent layer 231*b*, where the wearer-facing layer 231*a* and the liquid impermeable barrier layer 231*c* extend beyond the absorbent layer 231*b* and the wearer-facing layer 231*a* is joined directly to the liquid impermeable barrier layer 231*c*, by adhesive, tape, thermal bonding, or a combination thereof, preferably tape, to form a liquid impermeable seal 232 around a perimeter of the absorbent layer 231*b*. As shown in FIG. 6A, the wearer-facing layer 231*a* of the absorbent front panel 230 may be joined directly to the liquid impermeable barrier layer 231*c* of the absorbent front panel 230 and the liquid impermeable barrier layer 231*c* of the absorbent front panel may be joined directly to the front waist portion 100 of the pant, by tape, to form a liquid impermeable seal 232 around a perimeter of the absorbent layer 231*b*. In other words, as shown in FIG. 6A, the wearer-facing layer 231*a* is superadjacent to the liquid impermeable barrier layer 231*c* and the liquid impermeable barrier layer 231*c* is superadjacent the pant in the liquid impermeable perimeter seal 232. The absorbent layer 231*b* may optionally be joined to the wearer-facing layer 231*a*, the liquid impermeable barrier layer 231*c*, or both, by adhesive 233, as shown in FIGS. 6A-6D.

The pant, preferably the front waist portion 100 of the pant, may comprise an absorbent panel comprising a wearer-facing layer 231*a*, an absorbent layer 231*b* disposed to the outward-facing side of the wearer-facing layer 231*a*, and a liquid impermeable barrier layer 231*c* disposed to the outward-facing side of the absorbent layer 231*b*, where the liquid impermeable barrier layer 231*c* extends beyond the absorbent layer 231*b* and the wearer-facing layer 231*a*. The liquid impermeable barrier layer 231*c* may be joined directly to the wearer-facing layer 231*a*, as shown in FIG. 6A. Preferably, the liquid impermeable barrier layer 231*c* is joined directly to the pant (e.g., by adhesive, tape, thermal bonding, or a combination thereof, preferably tape), as shown in FIG. 6A. As shown in FIG. 6A, the wearer-facing layer 231*a*, the absorbent layer 231*b*, and liquid impermeable barrier layer 231*c* of the absorbent front panel may be joined to the front waist portion 100 of the pant, by tape, to form a liquid impermeable seal 232 around a perimeter of the wearer-facing layer 231*a*, the absorbent layer 231*b*, and/or the liquid impermeable barrier layer 231*c*. As shown in FIG. 6A, the liquid impermeable barrier layer 231*c* is superadjacent the pant 10 in the liquid impermeable perimeter seal 232. The absorbent layer 231*b* may optionally be joined to the wearer-facing layer 231*a*, the liquid impermeable barrier layer 231*c*, or both, by adhesive 233, as shown in FIG. 6A.

Figure 6B:
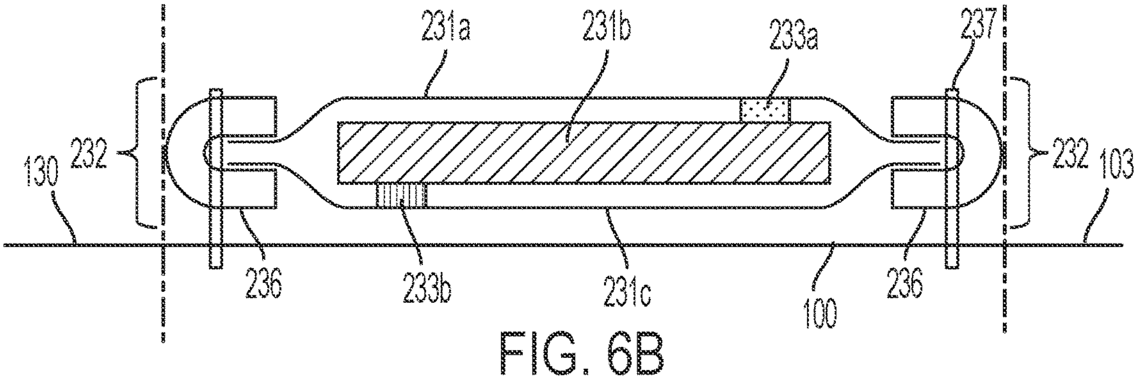

Alternatively, the pant 10, preferably the front waist portion 100 of the pant 10, may comprise an absorbent panel, as shown in FIG. 5A, comprising a wearer-facing layer 231*a*, an absorbent layer 231*b* disposed to the outward-facing side of the wearer-facing layer 231*a*, and a liquid impermeable barrier layer 231*c* disposed to the outward-facing side of the absorbent layer 231*b*, where the wearer-facing layer 231*a* and the liquid impermeable barrier layer 231*c* extend beyond the absorbent layer 231*b* and the wearer-facing layer 231*a* is joined directly to the liquid impermeable barrier layer 231*c*, by a C-folded tape, to form a liquid impermeable seal 232 around the perimeter of the absorbent layer 231*b*. The absorbent panel may then be joined to the pant 10, preferably to the front waist portion of the pant, by adhesive, tape, thermal bonding, stitching (as shown in FIG. 6B), or a combination thereof, preferably tape.

Figure 6C:
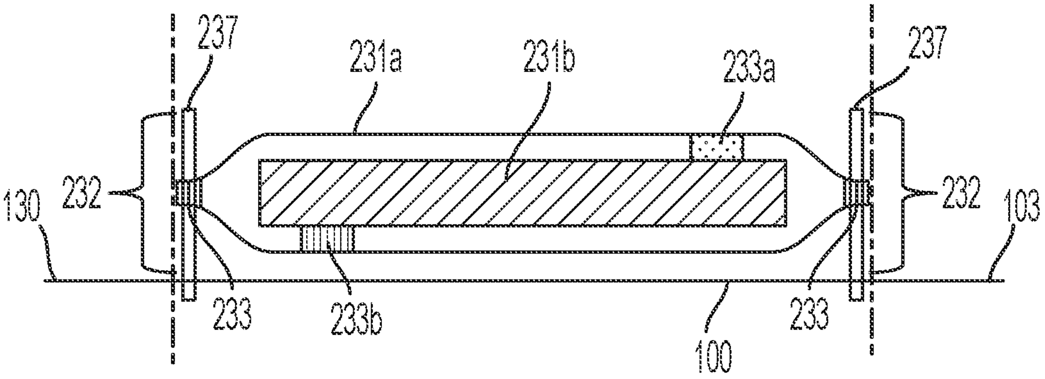

Alternatively, the pant 10, preferably the front waist portion 100 of the pant 10, may comprise an absorbent panel, as shown in FIG. 5B, comprising a wearer-facing layer 231*a*, an absorbent layer 231*b* disposed to the outward-facing side of the wearer-facing layer 231*a*, and a liquid impermeable barrier layer 231*c* disposed to the outward-facing side of the absorbent layer 231*b*, where the wearer-facing layer 231*a* and the liquid impermeable barrier layer 231*c* extend beyond the absorbent layer 231*b* and where the wearer-facing layer 231*a* is joined directly to the liquid impermeable barrier layer 231*c* by an adhesive 233 to form a liquid impermeable seal 232 around the perimeter of the absorbent layer 231*b*. The absorbent panel may then be joined to the pant, preferably to the front waist portion of the pant, by adhesive, tape, thermal bonding, stitching (as shown in FIG. 6C), or a combination thereof, preferably tape.

Figure 6D:
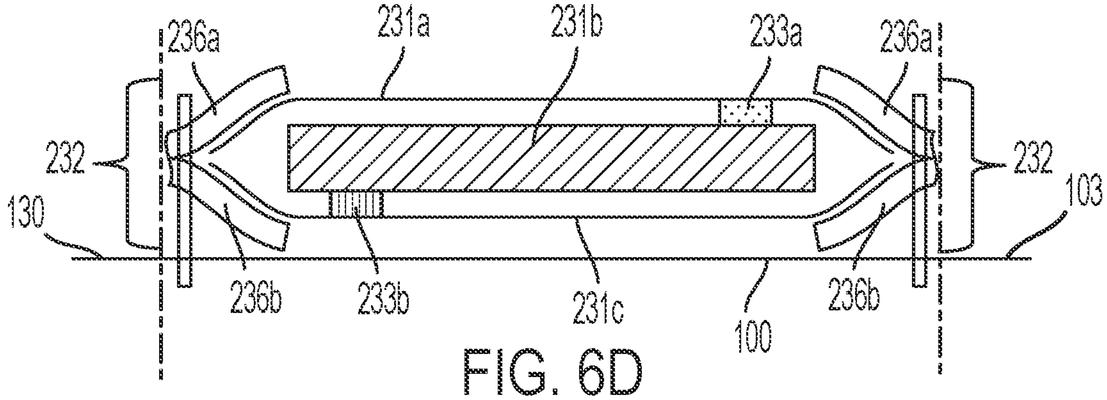

Alternatively, the pant, preferably the front waist portion 100 of the pant, may comprise an absorbent panel, as shown in FIG. 5C, comprising a wearer-facing layer 231*a*, an absorbent layer 231*b* disposed to the outward-facing side of the wearer-facing layer 231*a*, and a liquid impermeable barrier layer 231*c* disposed to the outward-facing side of the absorbent layer 231*b*, where the wearer-facing layer 231*a* and the liquid impermeable barrier layer 231*c* extend beyond the absorbent layer 231*b* and where the wearer-facing layer 231*a* is joined directly to the liquid impermeable barrier layer 231*c* to form a liquid impermeable seal 232 around the perimeter of the absorbent layer 231*b* by a first tape 236*a* and a second tape 236*b*, the first tape 236*a* being joined to the wearer-facing layer 231*a* and the second tape 236*b* and the second tape 236*b* being joined to the liquid impermeable barrier layer 231*c* and the first tape 236*a*, preferably provided that the first tape 236*a* and the second tape 236*b* do not overlap the absorbent layer 231*b*. The absorbent panel may then be joined to the pant, preferably to the front waist portion of the pant, by adhesive, tape, thermal bonding, stitching (as shown in FIG. 6D), or a combination thereof, preferably tape. When stitching 237 is used to join the absorbent panel to the pant, as shown in FIG. 6D, the stitching does not puncture the liquid impermeable barrier layer 231*c*.

Alternatively, the pant 10, preferably the front waist portion 100 of the pant 10, may comprise an absorbent panel comprising an absorbent layer 231*b* and a liquid impermeable barrier layer 231*c* disposed to the outward-facing side of the absorbent layer 231*b*, where the absorbent layer 231*b* is the wearer-facing layer, where the absorbent layer 231*b* and/or the liquid impermeable barrier layer 231*c* are joined to the pant, preferably to the front waist portion of the pant, by adhesive, tape, thermal bonding, stitching, or a combination thereof, preferably tape, to form a liquid impermeable seal 232 around the perimeter of the absorbent layer 231*b*, the perimeter of the liquid impermeable barrier layer 231*c*, and/or both, as shown in FIGS. 7A and 7B. The absorbent layer 231*b* may also be joined to the liquid impermeable barrier layer 231*c* by adhesive 233, as shown in FIGS. 7A and 7B. The liquid impermeable barrier layer 231*c* may extend beyond the absorbent layer 231*b*, as shown in FIG. 7B.

Attachment/Joining Mechanism

In constructing the absorbent panels and/or durable absorbent pants disclosed herein, a variety of attachment/joining mechanisms, such as stitching/sewing, adhesive bonding, and thermal bonding (fusing or welding), may be used. In the context of adhesive bonding, a tape may be used.

Suitable tapes include heat sealing tapes, which are known in the textile industry for reinforcing an area, seam, edge, or opening and/or provide waterproofing to seams and edges, e.g., seam reinforcement tapes, edge sealing tapes, water proofing tapes, sew-free tapes, heat seaming tapes, heat tapes, and adhesive tapes. Heat sealing tapes may be selected to be stretchable, low profile, comfortable next to skin, breathable, durable through hot wash and drying cycles, and hydrophobic.

Tape generally comprises an adhesive disposed on a backing layer. The adhesive may be selected to bond to a particular surface or surfaces, such as natural fibers, synthetic fibers, or blends thereof. Adhesive may also be selected for durability through multiple washing (e.g., at 60° C. or greater) and drying cycles, stretch properties, and breathability. Adhesive may be disposed on the backing layer in a selected pattern. The pattern may be selected to, for example, enhance the breathability of the tape. The adhesive may be a polyurethane adhesive. The adhesive thickness may range from about 25 microns to 50 microns. The tack temperature and activation temperature of the adhesive may also be selected and optimized to bond to a particular surface or surfaces, such as natural fibers, synthetic fibers, or blends thereof. The temperatures to heat press or tack and to seal can range from about 90° C. to about 700° C. More than one type of tape can be used to construct the absorbent panels and/or durable absorbent pants disclosed herein. The backing layer of the tape may be a polymer film, e.g., a silicone-based polymer film, a non-woven, a woven, or a knit. Fabric backing layers generally weigh from about 100 to about 400 gsm.

The tape may be stretchable and exhibit various stretch properties, depending on the stretch properties of both the adhesive and the backing layer of the tape. The tape may have a modulus at 50% elongation of about 1.0 to 20 N/10 mm. The tape may have a recovery from stretching to 50% elongation of a 10 cm length ranging from about 50% to about 99% of the original value. Tape can be provided in sheet form (e.g., continuous or discontinuous sheets) or strips of particular width. A strip of tape having a width of about 3 mm to about 30 mm may be used.

Length

The absorbent front panel 230 may extend longitudinally the entire overall length L of the pant (or, when the pant comprises a waist band 103, to the edge of the waist band 103*a*, or to a location underneath the waistband in the case of a Y split waistband). However, it has been found that when the absorbent front panel 230 extends the entire overall length L of the pant or less than the entire overall length L of the pant but to the lateral axis 300, wearer comfort is adversely affected and the pant may be less discreet under clothing. Thus, the maximum length of the absorbent front panel 230 $PL_{max}$ may vary. The absorbent front panel 230 may extend from the front waist edge 102 to the lateral crotch tangent line 500, as suggested by the dashed-line portions of FIG. 1, and the absorbent front panel 230 may have a maximum length $PL_{max1}$. The absorbent front panel 230 may extend from the edge of the waist band 103*a* to an absorbent front panel minimum rear extent 402 and the absorbent front panel 230 has a maximum length $PL_{max2}$. The absorbent front panel may extend into the rear waist portion 120 (not shown).

The absorbent front panel 230 may have a maximum length $PL_{max}$ that is from about 1% of the length L of the pant to about 95% of the length L of the pant, preferably from about 10% of the length L of the pant to about 75% of the length L of the pant, more preferably from about 20% of the length L of the pant to about 60% of the length L of the pant, even more preferably from about 25% of the length L of the pant to about 50% of the length L.

Width

It has been learned through experimentation that typical durable absorbent brief pants, currently marketed to wearers experiencing incontinence, do not have an absorbent front panel width that is sufficient for providing effective coverage, while maintaining contact against the body through a variety of normal body positions and movements. Accordingly, it may be desired that the maximum width $PW_{max}$ of the absorbent front panel 230 is greater than or equal to the smallest width dimension CW measured between the crotch leg opening edges 140. The absorbent front panel 230 may have a maximum width $PW_{max}$ (see FIGS. 1, 2) that is from about 5% of the maximum width W max of the pant to about 95% of the maximum width $W_{max}$ of the pant, preferably from about 15% of the maximum width $W_{max}$ of the pant to about 85% of the maximum width $W_{max}$ of the pant, more preferably from about 20% of the maximum width $W_{max}$ of the pant to about 75% of the maximum width $W_{max}$ of the pant, even more preferably from about 20% of the maximum width $W_{max}$ of the pant to about 35% of the maximum width $W_{max}$ of the pant.

Caliper

Caliper is the thickness in the z-direction of the garment at any location. For purposes of minimizing bulk, it may be desired that the combination of layered materials in the absorbent front panel 230 have a maximum Caliper less than or equal to about 10 mm, preferably less than or equal to about 5 mm, more preferably less than or equal to about 4 mm, and even more preferably less than or equal to about 3.5 mm and greater than or equal to about 0.5 mm. “Central z-direction Caliper” or “central Caliper” is measured at the geometrical center point of the absorbent front panel 230 with respect to the longitudinal axis and lateral axis (when opened and laid out flat on a horizontal planar surface). Preferably, maximum Caliper and central Caliper are measured on a flat region of the absorbent panel that does not comprise any seams or tapes. Based on disclosure herein and teachings available in the art concerning textiles, persons of ordinary skill in the art will be equipped to select a combination of suitable materials to create a structure in the absorbent front panel 230 having such Caliper, along with other features and attributes described herein.

Absorption Capacity

In order for a durable absorbent pant to provide suitable absorbency and protection against leakage of unintended discharges of urine over a reasonable duration of wear, for a man experiencing light to moderate incontinence, while balancing concerns for limiting caliper/bulkiness of the front waist portion 100 and the required relative planar size/surface area of the absorbent front panel, it may be desired that a combination of material forming the absorbent front panel 230 of the pant may have an Area Absorption Capacity from 0.1 ml/$cm^2$ to 1.0 ml/$cm^2$ and/or a Volume Absorption Capacity from 0.4 ml/$cm^3$ to 0.8 ml/$cm^3$, measured according to the Absorption Capacity Measurement method set forth below. Based on disclosure herein and teachings available in the art concerning textiles, persons of ordinary skill in the art will be equipped to select a combination of suitable materials to create a front absorbent panel 230 having such absorption capacity. It is believed, further, based on recent availability of fabric materials including yarns that include superabsorbent polymers (e.g., fabrics including “SAF” superabsorbent fiber, as available from Technical Absorbents Limited, Grimsby, United Kingdom), that a front absorbent panel 230 may be configured to have a Volume Absorption Capacity greater than 0.8 ml/$cm^3$, e.g., up to 0.9 ml/$cm^3$, 1.0 ml/$cm^3$, 1.1 ml/$cm^3$, or even up to 1.2 ml/$cm^3$. Without intending to be bound by theory, it is believed that materials such as these can provide Volume Absorption Capacity at such levels by swelling beyond their dry volumes, with absorbed liquid.

Stretch Attributes

Through experimentation it has been learned that imparting a pant with appropriate directional stretch characteristics within the absorbent front panel 230 are important to provide a pant that is both comfortably and securely held against the wearer’s body surfaces, in position to intercept and absorb the flow of urine, and thereby prevent leakage from the pant, through normal ranges of body positions and movements. It has been learned that the combination of materials present in the absorbent front panel 230 preferably should exhibit a maximum Longitudinal Elongation of 10 percent to 100 percent, measured according to the Maximum Elongation Measurement Method set forth below. Alternatively, or additionally, it may be desired that the combination of materials present in the absorbent front panel 230 exhibit a Longitudinal Tensile Modulus, measured according to the Longitudinal Tensile Modulus Method set forth below (reflecting the presence of one or more materials that impart elasticity) of 10 gf/mm to 150 gf/mm. Based on disclosure herein and teachings available in the art concerning textiles, persons of ordinary skill in the art will be equipped to select a combination of suitable materials to create an absorbent front panel 230 that has such longitudinal elongation and tensile modulus properties.

Materials Selection

Generally, the front and rear waist portions 100, 120 of suitable examples of a pant may be formed of any fabric material or combination of fabric and other materials known and used as components of underwear, swimwear or athletic/active wear, exhibiting suitable attributes that may include, depending upon the location of the fabric within the structure, pleasing feel against the skin (softness and/or low-friction/smooth/silky feel), low caliper/bulk, elongation capability, elasticity, absorbency, wicking ability, breathability, etc.

The absorbent front panel 230, as herein described requiring absorbency and longitudinal elastic stretch attributes, may include a combination of several materials selected to impart the absorbent front panel 230 with the desired attributes.

Fabric Structure

Most durable fabrics exhibit anisotropic elongation capabilities.

Woven fabrics, formed by weaving, are formed of two groups (warp group and weft group) of interlaced constituent yarns or threads, the yarns or threads within each group being substantially parallel to each other, and substantially perpendicular to the yarns or threads in the other group, along the plane of the fabric. Unless the constituent yarns or threads are themselves formed of elastic material, woven materials have relatively low elongation capabilities along the warp and weft directions and have relatively higher elongation capabilities along the two bias directions approximately 45 degrees from the warp and weft directions. Consequently, where it is desired for particular reasons that a layer component of the absorbent front panel 230 be a woven material, it may be desired that the material be oriented within the absorbent front panel 230 such that one of the warp and weft directions is oriented from approximately 30 degrees to approximately 60 degrees, preferably from approximately 38 degrees to approximately 52 degrees, and more preferably approximately 45 degrees from the longitudinal direction of the pant, so as to provide maximum available longitudinal elongation capability for the woven layer.

However, when stretched along the bias direction, woven fabrics typically exhibit a substantial Poisson effect contraction along the trans-stretch direction (90 degrees from the stretch direction). When such a fabric is included in the absorbent front panel 230 with its bias oriented approximately along the longitudinal direction of the pant, the Poisson contraction effect may cause the absorbent front panel 230 to laterally narrow, which may be deemed undesirable when full coverage of the male genitalia is desired.

The constituent yarns or threads of knitted fabrics, by contrast, do not follow straight paths along the plane of the fabric, and are neither parallel nor perpendicular to each other. Rather, each constituent yarn or thread of a knitted fabric follows a looping path along successive rows, interlooping with one or more constituent yarns or threads in adjacent rows. As a consequence, knitted fabrics exhibit relatively greater elongation capability along all directions as compared with woven fabrics, even where the constituent yarns or threads themselves are not elastic. For this reason, unless a woven fabric is desired for a particular reason, it may be preferred that a knitted fabric be used to form any one or more, or all, of the fabric layers present in the absorbent front panel 230 of the pant.

Even so, most types of knitted fabrics have elongation capabilities that are anisotropic along the plane of the fabric, having a first direction of greatest elongation capability and a second direction, perpendicular to the first direction, of least elongation capability. Accordingly, when knitted fabric is selected and used to form one or more layers present in the absorbent front panel 230 of the pant, it may be desired that the fabric(s) forming any, some, or all of the layers be oriented such that their directions of greatest elongation capability are at least approximately parallel with the longitudinal direction of the pant.

In some circumstances it may be desired that a knitted fabric selected to form a layer be a rib knit type. Rib knitted fabrics exhibit relatively high elongation capability along a direction parallel to the knit rows (perpendicular to the "ribs"), with relatively low Poisson contraction effect along the trans-stretch direction. Thus, in some circumstances, it may be desired that one or more layers present in the absorbent front panel 230 of the pant be formed of a rib knit fabric, with the "ribs" oriented substantially along the lateral direction of the pant.

In some circumstances it may be desired that the absorbent layer be formed of either woven or knitted terrycloth, for purposes of increasing aggregate fiber surface area and capillarity per unit fabric surface area, and thereby, providing increased absorbency to the absorbent layer 231*b*, while still providing a durable fabric, in contrast to a nonwoven batt or matt of fibers. In conjunction therewith or as an alternative, and for purposes of enhancing absorbency, it may be desired that constituent fibers of the yarn(s) or thread(s) from which the absorbent layer fabric material is knitted or woven be in the form of microfibers (i.e., fibers having an average denier of one (1) or less). It may be further desired that the constituent fibers be split microfibers. Yarns or threads formed of microfibers, particularly split microfibers, provide relatively greater fiber surface area per unit yarn/thread denier. When the fiber surfaces are hydrophilic, this imparts relatively greater absorbency to the fabric.

Fabrics Constituent Yarn/Thread Compositions

As contemplated herein, wearer-facing 231*a* and absorbent 231*b* layers present in the absorbent front panel of the pant are expected to be exposed to discharges of urine, and are expected to receive, absorb and retain the urine for a reasonable duration of wear time, preferably while leaving the wearer-facing surfaces as dry-feeling as possible. It may be desired that a wearer-facing layer 231*a* have a soft feel against the skin.

Accordingly, it may be desired that the wearer-facing layer be formed of a material that has a soft feel and has suitable wicking attributes so as to efficiently conduct discharged urine to an absorbent layer beneath, while having minimized tendency to retain urine and thereby have a wet feel for the wearer. Suitable materials may include polyesters and polyamides (e.g., nylon). Examples of these materials, when used to spin fiber components and/or when having received suitable hydrophilizing treatment, impart the spun fibers with suitable hydrophilic surface attributes (enhancing wicking), with relatively low individual fiber texture (reducing porosity and capillarity, and therefore, absorbency of the fabric). Additional materials may be incorporated in yarn or thread components for purposes of enhancing skin feel (e.g., enhancing a slick or silky feel against the skin) and/or further affecting hydrophilicity and/or reducing absorption tendencies. In some examples, polypropylene and/or polyethylene fiber components may be included for these purposes. In some examples, resins from which constituent fibers are spun may include additives to the primary polymer components, incorporated for enhancing skin feel, surface friction, adjusting hydrophilicity, reducing absorbency, etc. In some examples, polyester or nylon component resins may include an additive comprising linolenic acid, to the extent of and as described in US 2017/0369698, for purposes of enhancing elongation and skin feel attributes, while reducing material usage and cost.

Although commercially processed cotton or other commercially processed natural fiber, or semi-synthetic, cellulose-derived materials such as rayon, may be used or included as the component material for the absorbent layer for their inherent absorbency attributes, these materials may have a tendency, undesirably, to retain constituents of urine and/or other discharged fluids following laundering. Accordingly, one or more of polyester, polyamide and/or combinations thereof may be preferred as component resins or even the main/predominate component resins from which fiber components of yarn or thread components of fabrics for the absorbent layer 231*b* are formed.

For purposes of imparting elasticity to layers present in the absorbent front panel 230 (particularly longitudinal stretch elasticity), it may be desired that yarn or thread components of one or more of the fabrics present include elastic fibers, yarns or threads. In some examples, elastic fibers, yarns or threads may be formed of or include elastane or spandex (such as LYCRA, currently available from The LYCRA Company, Wilmington, Delaware), which are particularly elastic and durable through a plurality of launderings, as compared to other elastic materials used to elasticize fabrics.

In other examples, one or more elastic polymer film layers distinct from the fabric layer(s) in the absorbent front panel 230 may be included.

An elastic polymer film layer may be formed of any suitable elastic polymer material. In some examples, an elastic film layer may be formed by extrusion, flame lamination, or other application of film resin in molten or semi-molten form onto a layer component fabric, whereby the molten resin partially penetrates the fabric and upon cooling forms a film that is partially mechanically enmeshed in and/or made integral with the fabric.

Liquid Impermeable Barrier Layer

When urine is absorbed in a fabric layer in the absorbent front panel 230, the liquid impermeable barrier layer 231*c* may prevent the absorbed urine from passing from the absorbent layer 231*b* to the pant 10 or even to the outer clothing. In some examples, the liquid impermeable barrier layer 231*c* may be formed of a hydrophobically treated fabric material. Hydrophobic treatments include cellophane, fluorine, or silicone-based treatments or films. The liquid impermeable barrier layer 231*c* may be formed of or include a suitable liquid impermeable polymer film. In some examples, the film composition may be selected to have elastic elongation capability, providing suitable elastic stretch attributes to the combination of layers present in the absorbent front panel 230. A liquid impermeable barrier layer 231*c* may comprise a film formed in whole or in part of a polyurethane- or polyester-based resin. A liquid impermeable barrier layer 231*c* may comprise a film that is formed by extrusion or other application of thermoplastic film resin in molten or semi-molten form directly onto the outward-facing surface of an overlying layer, such as absorbent layer 231*b*, such that the film resin while still molten partially penetrates the fabric and thereby forms a liquid impermeable film that is partially mechanically enmeshed in and/or made integral with the fabric. This also has the effects of consolidating layers, which can reduce caliper in the absorbent front panel 230 and reducing or preventing wrinkling or bunching of the absorbent layer 231*b* upon elastic contraction. A polyurethane or polyester film may be formed by extrusion or other application of molten thermoplastic resin directly onto an outward-facing surface of a fabric that serves as or forms a component of absorbent layer 231*b*.

The material selected for the liquid impermeable barrier layer 231*c* may also be vapor permeable or "breathable" in that it can permit gas or water vapor to pass therethrough, while still being effectively liquid impermeable under ordinary conditions of the use contemplated herein, via a combination of having a porous structure for vapor permeability, but sufficiently small pore sizes and surfaces having low wettability (e.g. hydrophobic surfaces), for liquid impermeability. Various liquid impermeable, vapor permeable films and other materials are known and used in fields including personal hygiene, garment, and wound dressing applications. A liquid impermeable but vapor permeable barrier layer may be preferred in some circumstances for purposes of venting water vapor to improve wearer comfort and/or help avoid overhydration of the wearer's skin. A monolithic thermoplastic elastomeric (TPE) film material may be desired for the liquid impermeable barrier layer 231*c*, for having stretch/elasticity characteristics and breathability.

It may also be desired that the material selected for the liquid impermeable barrier layer 231*c* be able to withstand application of heat, where used to bond the liquid impermeable barrier layer 231*c* to an overlying fabric layer, such that the material will not develop holes therethrough during the bonding process (which can compromise liquid impermeability). A suitable liquid impermeable barrier layer 231*c* material for the above-mentioned purposes may include polyethylene terephthalate (PET), or thermoplastic polyester elastomer (TPEE). The material may be obtained in the form of a monolithic film and may be applied and bonded to a fabric layer via application of heat.

Antimicrobial Agents

For purposes of hindering growth of microorganisms supported by absorbed urine, which may cause odor, it may be desired to include one or more antimicrobial agents in or among the materials present in the absorbent front panel 230 and/or in any other element of the pant, such as the front waist portion 100, the crotch portion 130, the rear waist portion 120, and/or the waist band 103. Any such antimicrobial agents are preferably included in a form adapted to remain in place and continue to be effective following a plurality of launderings of the pant. In some examples, an antimicrobial agent may include particles of a metal, metal alloy or metallic compound that includes one or more of copper, silver, zinc, aluminum or combinations thereof. In other examples an antimicrobial agent may include particles of carbon or a composition or compound including carbon. One or more of these materials may be included as additives to resins from which constituent fibers are spun, or may be included in compositions that are topically applied to constituent yarns, threads or fabrics following manufacture thereof. Such antimicrobial agents are preferably included in material(s) forming the absorbent layer 231*b* and/or the wearer-facing layer 231*a*.

Other Construction Details

Figure 4B:
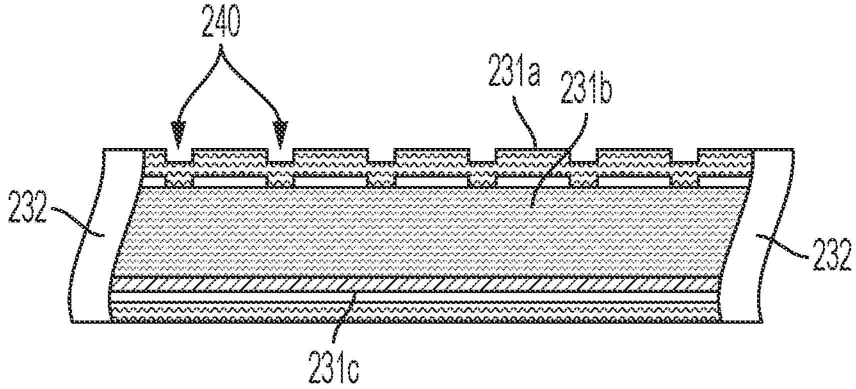
FIG. 4B is a magnified schematic lateral cross section of an example of an absorbent front panel as depicted in FIG. 4A, taken along line 4-4.

In some examples one or more layers within the absorbent front panel 230 may be bonded together via any suitable bonding mechanism. Referring to FIGS. 5A-5C, for example, a wearer-facing layer 231*a* may be bonded to a subjacent absorbent layer 231*b* for purposes of holding the layers in close proximity and thereby helping maintain a desired low caliper of the structure, and enhancing fluid communication between the layers, i.e., enhancing the structure's ability to pass discharged urine from the wearer-facing layer to the underlying absorbent layer, via contact between the layers. In such example, the bonding mechanism should be selected so as not to occlude the interface between the two layers along any substantial portion of their interfacing surface areas. Thus, in some examples it may be desired that the bonding mechanism have the form of a discontinuous pattern of discrete bonds (i.e., a pattern with unbonded regions between the bonds), such as a regular pattern of spot bonds 240, as shown in FIG. 4B. In some examples, bonds between the layers may be formed by discrete deposits of adhesive between the layers, adhering them together at the locations of the deposits. In other examples, bonds between the layers may be formed by thermal compression bonding. The latter bonding mechanism may be more durable through a plurality of launderings, and as illustrated schematically in FIG. 4B, creates a corresponding pattern of z-direction depressions in the wearer-facing layer 231*a* that may serve to collect discharged urine/fluid and initiate and/or facilitate its movement (via wicking) down to the absorbent layer 231*b*. For purposes of enabling thermal compression bonding, the wearer-facing layer and the subjacent absorbent layer may each include polymer components of respective fusible compositions (such as similar polyester-based compositions) that facilitate formation of robust bonds between the layers upon localized application of heat and pressure at the bond sites. (Herein, "fusible compositions," with respect to two respective polymers present in two respective layers, means that the two polymers are miscible, capable of melting and mixing at a temperature of 250° C. or lower, to form a single thermodynamic phase.)

Various layers that may be included in absorbent front panel 230, e.g., layers 231*a*, 231*b*, 231*c*, may also be joined to each other and/or to a layer(s) of the front waist portion 100, the crotch portion 130, and/or the rear waist portion 120 by any suitable mechanism. The joining mechanism may be a system of stitching to affix the layers together; however, for purposes of liquid containment it may be desired that the joining mechanism include a generally hydrophobic, water insoluble adhesive, by itself or as a supplement to stitching. Water proof tapes may also be used as joining mechanisms to bring the materials together, seal-edged, and/or to join the absorbent front panel 230 to the front waist portion 100.

EXAMPLES

Quantities of prototype brief pants were manufactured to include an absorbent front panel, having the following layers, in order of wearer-facing (upper) layer to outward-facing (lower) layer:

- Wearer-facing layer: Knitted fabric, 66% polyester, 34% polypropylene; direction of greatest elongation oriented longitudinally;
- Absorbent layer: Knitted sheared pile terrycloth/sheared pile fabric, 86% polyester microfiber yarn, 14% nylon microfiber yarn; nylon yarn treated with antimicrobial agent including copper particles; sheared pile side facing wearer; direction of greatest elongation oriented longitudinally; and
- Liquid impermeable barrier layer: Polyurethane film, extruded onto outward-facing surface of absorbent layer; and
- Outward-facing layer: knitted fabric, 76% nylon, 24% elastane.

A useful method for characterizing the feel and stiffness of fabric and textile materials is to measure the hand or handle of a material using a Handle-O-Meter, which measures the combined effects of flexibility and surface friction of sheeted materials, including nonwovens, tissue, toweling, film and textiles. A suitable instrument is a Handle-O-Meter Model No. #211-300, manufactured by Thwing-Albert Instrument Co, West Berlin, NJ, or equivalent.

A modification to the test procedure ASTM D 6828-02 is used as described herein. A 100 g beam with a 20 mm slot opening is used. All samples are cut from the absorbent front panel of the garment. First, the full absorbent front panel is extracted from the garment, where the absorbent front panel of the garment is defined as the portion that includes a barrier material within the layers to prevent liquid breakthrough. If the absorbent front panel has seams or is otherwise non-flat, the seams are cut to enable the absorbent panel to lay flat. The sample is cut from the absorbent front panel of the garment including all layers of the garment using a steel rule cutting die to cut a sample 80 mm in length and 20 mm in width. This rectangular sample is cut from the absorbent front panel with the long side oriented perpendicular to the waist band of the absorbent garment and generally centered in the absorbent front panel with respect to the boundaries of the absorbent front panel such that edges, seams, tapes, etc. are not included in the 80 mm×20 mm cut sample. The cut sample is laid flat on a testing plate. The order and orientation of each layer is preserved in the sample as each layer is present in the absorbent garment, such that a sample is cut with a wearer-facing side and an outward-facing side. Four (4) samples are cut for each analysis from corresponding sites on four replicate articles. Two samples are tested with wearer-facing side up, and two samples are tested with wearer-facing side down, such that the long side of the sample spans the 20 mm slot opening and is centered with nearly equal lengths of the sample extending on either side of the slot, centered under the beam in the center of the plate. The average grams force divided by the total sample width is reported for each specific orientation to the nearest 0.1 gf/mm. If a sample measures less than 1 gf upon running the method, then a second or third or fourth sample may be added and placed alongside the first sample in identical orientation, so as to extend the effective width that is tested. In any case, the grams force is always divided by the total width tested (e.g., 20 mm, 40 mm, 60 mm, 80 mm) and reported as gf/mm width.

It is believed that handle correlates with a wearer's assessment of comfort, including the degree to which a textile material deforms and buckles, when the body is moving. Lower handle values, e.g., about 0.1 gf/mm to about 10.0 gf/mm, represent materials that are flexible when used in absorbent garments. Materials having a handle of about 11 gf/mm or greater are more rigid in bending and tend to buckle, creating undesirable folds and a worse fit to the body. By smoothly integrating the absorbent front panel into the pant, as described herein, it is believed that absorbent front panels exhibiting handle values of about 0.1 to about 10 gf/mm, or about 0.2 gf/mm to about 6 gf/mm, or about 0.3 gf/mm to about 3 gf/mm may provide acceptable comfort in wear. On the contrary, it is believed that when the absorbent front panel is not smoothly integrated into the pant in accordance with the present disclosure, the handle of the absorbent front panel may need to be more narrowly selected to provide acceptable comfort in wear.

Figure 10:
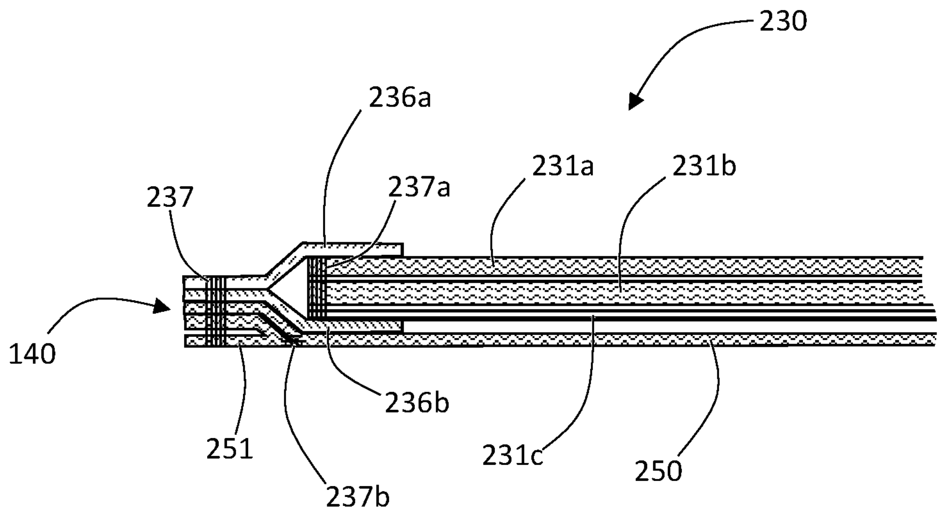
FIG. 10 is a schematic lateral cross section of an example of a brief pant through a portion of the crotch portion including an absorbent panel and a leg opening edge thereof.

In addition to the configurations described above and illustrated in FIGS. 1-9C, materials and components may be adapted, configured, assembled and/or combined in the following manner, illustrated in FIG. 10:

In the example depicted in FIG. 10:

The top sheet/wearer-facing layer 231*a*, absorbent layer 231*b*, back sheet/barrier layer 231*c*, first body fabric 250, second body fabric 251 and stitching materials (at stitches 237, 237*a* and 237*b*) may be any materials identified or described in the description hereinabove, to constitute or form these components, or alternatively, may be other materials.

The first and second tape materials 236*a*, 236*b* are each a laminate of a fabric strip facing out and an adhesive strip facing in. The first and second tape materials 236*a*, 236*b* are adhered together proximate the leg opening edge 140, and, respectively, adhered to wearer-facing layer 231*a* on the wearer-facing surface thereof, and adhered to the barrier layer 231*c* on the outward-facing surface thereof. Serge stitching 237*a* holds layers 231*a*, 231*b* and 231*c* together along perimeter edges thereof. The tapes materials 236*a*, 236*b*, respectively, cover serge stitching 237*a* on the wearer-facing surface of the wearer-facing layer 231*a* and the outward-facing surface of the barrier layer 231*c*, and serve to seal the stitching 237*a* and edges of the absorbent panel 230 to prevent wicking and leakage from the absorbent layer and/or wearer-facing layer proximate the leg opening edge 140.

Stitching 237 may be included to secure the absorbent panel 230 to the outer body fabric 250, through the tape materials 236*a*, 236*b* as shown. An added strip of body trim fabric 251 may be included where shown in FIG. 10 to provide more consistent caliper to the assembly proximate the leg opening edges and a more finished appearance, and may be held in place by stitching 237, 237*b*.

Measurement Methods

General Sample Preparation

Unless otherwise specified below, each of the measurements below is to be conducted on 1-3 separate like samples (taken from 1-3 separate like examples of pants) and the average of the 1-3 separate like samples is considered to be the measurement for that specific sample set.

Samples including the entire absorbent front panel 230 are collected from examples of the subject pant. The pant is cut apart along the left 401*b* and right 401*c* lateral edges of the absorbent front panel 230 and along the minimum rear extent 402 of the absorbent front panel 230 (see FIG. 2) (without cutting into the seams themselves) to provide a sample that includes the entire absorbent front panel 230, including the liquid impermeable seal 232.

If the pant is a legged pant, cut out the absorbent front panel in its entirety, along cutting paths outside of the seam(s) joining the absorbent front panel to the remainder of the pant, without cutting into the seams themselves.

The sample should be cut from the example pant with a sharp knife or suitably sharp cutting device effective to precisely and cleanly cut the sample. A straight edge or other suitable drafting/drawing tool may be used where helpful to hold the example down on the work surface and help guide the cutting device.

The testing is performed under ambient room conditions (temperatures from between 15° C. to 35° C. and relative humidity from between 35% to 75%). Samples are conditioned for at least two hours prior to testing under the same conditions.

All linear dimensions are measured manually by ruler within the ordinary x-y plane, using a ruler that is traceable to NIST or other standards organization.

Longitudinal Tensile Modulus

For the Longitudinal Tensile Modulus and Maximum Longitudinal Elongation test methods, the samples as described above in "General Sample Preparation" are further modified by cutting out a 40 mm laterally wide section symmetrically about the longitudinal axis 200, being careful not to include a seam or tape within the cut sample.

The Longitudinal Tensile Modulus of the sample is determined by stretching along the direction of the longitudinal axis 200 of the pant, using a constant rate of extension tensile testing machine with computer interface, e.g., Instron; MTS; Zwick; etc., using a load cell for which the loads measured are within 10% to 90% of the limit of the cell, and ensures accuracy of a 5N load to 0.1N. The instrument is equipped with a single line contact grips, 8 cm in grip width. Prior to testing, calibrate the equipment according to the instruments manufacturer's recommendations.

In accordance with the sample preparation instructions set forth above, the Sample Width is 40 mm. The stress in the sample is calculated by dividing the force in the load cell by the Sample Width, and is expressed in units of gf (grams-force)/mm. (The caliper of the sample is not a factor in this calculation.) The Sample Length is equal to 80 mm.

The grips of the tensile testing machine consist of air actuated grips designed to hold the sample. No slippage should be permitted between the sample and the grips. The distance between the grips (along the axis of the machine's elongation) should be the Sample Length minus 6 cm. This distance will be hereinafter referred to as the "Starting Gauge-Length".

The sample is mounted in the grips with its longitudinal axis 200 parallel to the direction of applied elongation, and centered in each grip. Two (2) cm of the sample's length at each end is inserted into each grip. The Starting Gauge Length, determined as described above, will ensure that 2 cm of longitudinal slack will be present in the sample at the start of the test.

After the sample is mounted, the machine's load channel is set to zero (this eliminates the weight of the sample in the calculations). The grips are slowly moved apart at 5.08 cm/min (2.0 in/min) until a load of 5 gf (grams-force) is reached. The separation between the grips at this position is recorded as L0.

$$(L0 = \text{Starting Gauge Length} + \text{additional machine extension to reach 5 gf})$$

After the 5 gf load is reached, extend the sample at a rate of 50.8 cm/min (20 in/min) with a data acquisition rate of 50 Hz. Extend until either a stress of 30 gf/mm is reached, or the sample breaks.

Sample strain is calculated by ΔL/L0. AL is any additional extension between the grips after L0 is reached and is recorded along with load at a rate of 50 Hz. Sample strain is expressed numerically (not as a percentage), thus a strain of 100% is 1.0 for the purposes of these calculations.

Record the sample strains at sample stresses of 10 gf/mm and at 20 gf/mm.

Longitudinal Tensile Modulus is the linear slope between 10 gf/mm and 20 gf/mm, and is calculated as:

$$\text{Longitudinal Tensile Modulus} = [20\text{ gf/mm} - 10\text{ gf/mm}]/[\text{sample strain at 20 gf/mm} - \text{sample strain at 10 gf/mm}]$$

Repeat for each of the samples.

Maximum Longitudinal Elongation

Maximum Longitudinal Elongation is measured during the Longitudinal Tensile Modulus test. The Maximum Longitudinal Elongation is the sample strain at a sample stress of 20 gf/mm. Maximum Longitudinal Elongation is expressed as a percent strain, e.g., a value of 1.0 strain from the Longitudinal Tensile Modulus method is expressed as 100% strain for Elongation.

Repeat and record the results for all samples. Calculate and record the average of the results when multiple samples are tested. The average will be the Maximum Longitudinal Elongation value for the subject pant design.

Absorption Capacity

The absorption capacity test measures the amount of liquid held within a test sample after specified times of immersion and vertical drainage. The amount of test liquid that is retained by the test sample is used to calculate and report the Area Absorption Capacity (milliliters (ml) of liquid per specimen area in square centimeters) and the Volume Absorption Capacity (in milliliters (ml) of liquid per specimen volume in cubic centimeters). All testing is performed in a room controlled at 23° C.±3° C. and 50%±2% relative humidity.

The test procedure follows compendial method WSP 010.1.R3 (12) part B (Liquid Absorptive Capacity) with modifications specified as follows. The test liquid is deionized water at room temperature (23° C.±3° C.; density 1.00 g/ml). For the weighing portions of the test, no cover glass is used as the test liquid is non-volatile. The overall dimensions of the wire gauze test specimen support is large enough (e.g. 12 inches by 12 inches) to accommodate the larger test sample size. The test sample may be cut from the absorbent front panel at a convenient size such as 70 mm by 85 mm thus different than what is suggested in the compendial method.

Prior to measuring absorption capacity, the examples of the pants of interest (prior to removal of samples therefrom) are washed in order to mimic in-use conditions and to follow the recommended "prior to use" instructions that accompany these types of pants (e.g. wash before use). The examples are placed into a mesh lingerie bag, and then placed into a high efficiency, front-loading washing machine (any convenient source) along with a single small/light load dosage of TIDE brand laundry detergent ("Original" designation; "HE" or other high efficiency washing machine designation; without additives such as FEBREZE, ODOR DEFENSE, OXI additives, bleach or bleaching additives or fabric softening additives) (product of The Procter & Gamble Company, Cincinnati, Ohio). The washer is set to delicate cycle using cold water. After the wash cycle, the examples are removed from the mesh bag and placed flat on a drying rack to air dry for about 12 hours. After air-drying, the examples are placed into a clothes dryer (any convenient source) set on the delicate cycle with very low heat for about 5 minutes or until dry to the touch.

Test samples are prepared as follows. The pre-washed and dried examples are equilibrated in a room controlled at 23° C.±3° C. and 50%±2% relative humidity for about 2 hours. Test samples are cut from the examples as described in the General Sample Preparation section herein.

The immersion and drainage procedure outlined in the compendial method is then followed with the modifications previously noted. Subtract the Dry Mass from the Wet Mass and record as Liquid Mass Absorbed to the nearest 0.01 grams. Since the density of deionized water is 1.00 g/ml, the Liquid Mass Absorbed is also recorded as Liquid Volume Absorbed to the nearest 0.01 ml. Divide the Liquid Volume Absorbed (ml) by the overall area ($cm^2$) of the test specimen and record as Area Absorption Capacity to the nearest 0.01 ml/$cm^2$. Now divide the Liquid Volume Absorbed (ml) by the volume of the test specimen (area×central caliper) and record as Volume Absorption Capacity to the nearest 0.01 ml/$cm^3$. (Note: For purposes herein the area and central caliper of the test specimen is measured with the test specimen in a dry condition following sample preparation as described above, and in accordance with the Caliper measurement method set forth below.)

In like fashion, repeat for a total of one to three replicate test specimens. Calculate the arithmetic mean for Area Absorption Capacity and Volume Absorption Capacity and report to the nearest 0.01 ml/$cm^2$ and 0.01 ml/$cm^3$, respectively.

Caliper

The Caliper of a sample including an absorbent front panel is measured as the distance between a reference platform on which the sample rests and a pressure foot that exerts a specified amount of pressure onto the sample over a specified amount of time. All measurements are performed in a laboratory maintained at 23° C.±2° C. and 50%±2% relative humidity.

Caliper is measured with a manually-operated micrometer equipped with a pressure foot capable of exerting a steady pressure of 0.5 kPa±0.01 kPa onto the test sample. The manually-operated micrometer is a dead-weight type instrument with readings accurate to 0.001 mm. A suitable instrument is Mitutoyo Series 543 ID-C Digimatic, available from VWR International, or equivalent. The pressure foot is a flat ground circular movable face with a diameter of 50 mm. The sample is supported by a horizontal flat reference platform that is larger than and parallel to the surface of the pressure foot. The system is calibrated and operated per the manufacturer's instructions.

Obtain a sample absorbent front panel by removing it from the pant, as described above. When excising the sample from the pant, use care to not impart any wrinkles into the layers or other distortion of the layers during the removal process. Samples are conditioned at 23° C.±2° C. and 50%±2% relative humidity for 2 hours prior to testing. To measure caliper, first zero the micrometer against the horizontal flat reference platform. Place the sample on the platform with the desired measurement location centered below the pressure foot. Gently lower the pressure foot with a descent rate of 1.0 mm+0.1 mm per second until the full pressure is exerted on the sample. Wait 5 seconds and then record the caliper of the sample to the nearest 0.01 mm. In like fashion, repeat for a total of one to three replicate samples. Calculate the arithmetic mean for the Caliper and report to the nearest 0.01 mm.

Liquid Impermeability

When there is a question concerning whether a particular pant has an absorbent front panel with a liquid impermeable barrier layer, this Liquid Impermeability test method may be used to measure a quantity of test liquid that will pass through a sample and enable determination whether there is a "liquid impermeable barrier layer" present in the absorbent front panel, according to the definition set forth in the description above.

The Liquid Impermeability test measures the quantity of liquid transferred through to the outward-facing side of a test specimen obtained from a pant after it is dosed with a prescribed volume of test liquid in order to simulate a liquid insult during actual use/wear of the pant.

All testing is performed in a room controlled at 23° C.±3° C. and 50%±2% relative humidity.

Prior to performing the measurement of this method, the examples of the pants of interest (prior to removal of samples therefrom) are washed in order to mimic in-use conditions and to follow the recommended "prior to use" instructions that accompany these types of pants (e.g. wash before use). The examples are placed into a mesh lingerie bag, and then placed into a high efficiency, front-loading washing machine (any convenient source) along with a single small/light load dosage of TIDE brand laundry detergent ("Original" designation; "HE" or other high efficiency washing machine designation; without additives such as FEBREZE, ODOR DEFENSE, OXI additives, bleach or bleaching additives or fabric softening additives) (product of The Procter & Gamble Company, Cincinnati, Ohio), or equivalent. The washer is set to delicate cycle using cold water. After the wash cycle, the examples are removed from the mesh bag and placed flat on a drying rack to air dry for about 12 hours. After air-drying, the examples are placed into a clothes dryer (any convenient source) set on the delicate cycle with very low heat for about 5 minutes or until dry to the touch.

Test samples are prepared as follows. The pre-washed and dried example pants are equilibrated in a room controlled at 23° C.±3° C. and 50%±2% relative humidity for about 2 hours. Test samples containing the entire absorbent front panel are removed from the examples as described in the General Sample Preparation section herein. Using scissors, the outermost fabric layer on the outward-facing side of the gusset is cut out along the entire absorbent front panel shape, inboard of the seams, using care so as not to cut into any of the edge seams present. Mark the dose location at the intersection of the midpoint of the longitudinal axis of the sample and a lateral axis positioned at the narrowest portion of the specimen.

For each test sample, a single layer of filter paper is cut to 10 cm by 2.54 cm. A suitable filter paper is Ahlstrom Grade 989 (available from Ahlstrom-Munksjo North America LLC, Alpharetta, GA), or equivalent. The test liquid is deionized water at room temperature (23° C.±3° C.).

Record the mass of one layer of pre-cut filter paper and record as Dry Massip to the nearest 0.0001 grams. Place the pre-weighed filter paper onto a flat horizontal work surface. Position the test specimen centered over the filter paper with the garment facing side of the specimen facing the paper. Using a volumetric pipette, apply a 1.0 ml dose of test liquid to the pre-marked dosing location as follows. The tip of the pipette is held about 3 mm above the surface of the test specimen, and the dose is applied slowly (about 30 seconds) to avoid splashing. As soon as the entire dose has been applied, start a 1-minute timer. After 1 minute has elapsed, remove the test specimen and record the mass of the filter paper as Wet Massip to the nearest 0.0001 grams. Subtract the Dry Massip from the Wet Massip and record as z-Direction Leakage to the nearest 0.0001 grams.

In like fashion, repeat for a total of three replicate test specimens. Calculate the arithmetic mean for z-Direction Leakage and report to the nearest 0.0001 g.

Ordinary X-Y Plane Dimensions

For purposes herein, when a length or width of a feature of a pant is specified, it is to be measured with the pant laid out flat on a horizontal planar surface (in an opened or assembled configuration, as appropriate) with the material of the pant smoothed out flat, but in a relaxed condition, not pulled or stretched along any planar direction.

In view of the foregoing disclosure, the following additional non-limiting examples are contemplated hereby:

1. A durable absorbent panel, comprising a wearer-facing layer 231*a*, an absorbent layer 231*b* disposed to the outward-facing side of the wearer-facing layer 231*a*, and a liquid impermeable barrier layer 231*c* disposed to the outward-facing side of the absorbent layer 231*b*, wherein the wearer-facing layer 231*a* and the liquid impermeable barrier layer 231*c* extend beyond the absorbent layer 231*b*, wherein the wearer-facing layer 231*a* is joined directly to the liquid impermeable barrier layer 231*c* to form a liquid impermeable seal 232 around a perimeter of the absorbent layer 231*b*, wherein the absorbent layer 231*b* is joined to the wearer-facing layer 231*a*, the liquid impermeable barrier layer 231*c*, or both, and wherein the absorbent panel is washable.
2. The durable absorbent panel of example 1, wherein the wearer-facing layer 231*a* is joined directly to the liquid impermeable barrier layer 231*c* by adhesive, tape, thermal bonding, or a combination thereof, preferably tape.
3. The durable absorbent panel of example 2, wherein the wearer-facing layer 231*a* is joined directly to the liquid impermeable barrier layer 231*c* to form a liquid impermeable seal 232 around the perimeter of the absorbent layer 231*b* by a C-folded tape.
4. The durable absorbent panel of example 2, wherein the wearer-facing layer 231*a* is joined directly to the liquid impermeable barrier layer 231*c* to form a liquid impermeable seal 232 around a perimeter of the absorbent layer 231*b* by a first tape 236*a* and a second tape 236*b*, wherein the first tape 236*a* is joined to the wearer-facing layer 231*a* and the second tape 236*b* and the second tape 236*b* is joined to the liquid impermeable barrier layer 231*c* and the first tape 236*a*, provided that the first tape 236*a* and the second tape 236*b* do not overlap the absorbent layer 231*b*.
5. The durable absorbent panel of example 2, wherein the tape comprises a stretchable tape.
6. The durable absorbent panel of example 2, wherein the wearer-facing layer 231*a* is joined directly to the liquid impermeable barrier layer 231*c* by an adhesive 233 to form a liquid impermeable seal 232 around the perimeter of the absorbent layer 231*b*.
7. The durable absorbent panel of example 1, wherein the absorbent panel is shaped and configured to conform to a non-ruled or non-planar surface.
8. The durable absorbent panel of example 1, wherein the absorbent panel comprises more than one absorbent layer, preferably wherein the absorbent layers are joined to each other.
9. The durable absorbent panel of example 2, wherein the tape has a width of about 5 mm to about 25 mm.
10. The durable absorbent panel of example 1, wherein the wearer-facing layer 231*a* is a knitted fabric material.
11. A durable absorbent pant comprising an absorbent front panel 230; a front waist portion 100 with a front waist edge 102, an optional waist band 103, and left and right front leg opening edges 104, the front waist portion 100 comprising the absorbent front panel 230; a rear waist portion 120 with a rear waist edge 122 and left and right rear leg opening edges 124; a crotch portion 130, the crotch portion bridging the front waist portion 100 and the rear waist portion 120; and left and right hip side portions 160 joining the front waist portion to the rear waist portion to form a waist opening with a waist opening edge comprising the front waist edge 102 and the rear waist edge 122, and left and right leg openings; wherein the absorbent front panel 230 extends longitudinally from near the front waist edge 102 or the edge 103*a* of the optional waist band 103 to a minimum rear extent 402 and laterally from a left lateral edge 401*b* to a right lateral edge 401*c*; wherein each of the front waist portion 100, rear waist portion 120, and crotch portion 130 comprises a knitted material; wherein the absorbent front panel 230 comprises a wearer-facing layer 231*a*, an absorbent layer 231*b* disposed to the outward-facing side of the wearer-facing layer 231*a*, and a liquid impermeable barrier layer 231*c* disposed to the outward-facing side of the absorbent layer 231*b*, wherein at least one of, preferably both of, the wearer-facing layer 231*a* or the liquid impermeable barrier layer 231*c* extends beyond the absorbent layer 231*b*, wherein the wearer-facing layer 231*a* is joined, directly or indirectly, to the liquid impermeable barrier layer 231*c* to form a liquid impermeable seal 232 around a perimeter of the absorbent layer 231*b*; wherein the absorbent front panel is joined to the durable pant by adhesive, tape, thermal bonding, stitching, or a combination thereof, preferably tape, and wherein the durable absorbent pant is washable.

12. The durable absorbent pant of example 11, wherein the wearer-facing layer 231*a* of the absorbent front panel is joined directly to the liquid impermeable barrier layer 231*c* of the absorbent front panel by adhesive, tape, thermal bonding, or a combination thereof, preferably tape.

13. The durable absorbent pant of example 11, wherein the absorbent layer 231*b* is joined to the wearer-facing layer 231*a*, the liquid impermeable barrier layer 231*c*, or both by adhesive.

14. The durable absorbent pant of example 11, wherein the wearer-facing layer 231*a* is joined directly to the liquid impermeable barrier layer 231*c* by a first tape and a second tape, wherein the first tape is joined to the wearer-facing layer 231*a* and the second tape and the second tape is joined to the liquid impermeable barrier layer 231*c* and the first tape, provided that the first tape and the second tape do not overlap the absorbent layer 231*b*, wherein the absorbent front panel is joined to the durable pant by stitching, through the first tape and the second tape, provided that the stitching does not puncture the liquid impermeable barrier layer 231*c*.

15. The durable absorbent pant of example 11, wherein the tape comprises a stretchable tape.

16. The durable absorbent pant of example of example 11, wherein the absorbent panel is shaped and configured to conform to a non-ruled or non-planar surface.

17. The durable absorbent pant of example 11, wherein the absorbent panel comprises more than one absorbent layer, preferably wherein the absorbent layers are joined to each other.

18. The durable absorbent pant of example 12, wherein the tape has a width of about 5 mm to about 25 mm.

19. The durable absorbent pant of example 11, wherein the wearer-facing layer 231*a* is a knitted fabric material.

20. The durable absorbent pant of example 11, wherein the absorbent front panel 230 is reversibly joined to the pant, preferably using Velcro, adhesive, or a combination thereof.

21. The durable absorbent pant according to example 11, wherein the absorbent front panel 230 is irreversibly joined to the pant, preferably using adhesive, stitching, thermal bonding, ultrasonic welding, or a combination thereof.

22. The durable absorbent pant of example 11, wherein the absorbent front panel has a Handle of about 0.1 gf/mm to about 2.0 gf/mm and an Area Absorption Capacity of about 0.1 mL/cm$^2$ to about 1.0 mL/cm$^2$.

23. The durable absorbent pant of example 11, wherein the absorbent front panel has a Handle of about 0.1 gf/mm to about 2.0 gf/mm and a Volume Absorption Capacity of about 0.1 mL/cm$^3$ to about 10.0 mL/cm$^3$.

24 The durable absorbent pant of example 11, wherein the absorbent front panel 230 has a central Caliper at the intersection (250) of the lateral and longitudinal axes of about 1.0 mm to about 5.0 mm.

25. The durable absorbent pant of example 11, wherein the absorbent front panel 230 exhibits a Volume Absorption Capacity of at least −0.5 ml/cm$^3$, up to 1.2 ml/cm$^3$.

26. A durable absorbent pant comprising an absorbent front panel 230; a front waist portion 100 with a front waist edge 102, an optional waist band 103, and left and right front leg opening edges 104, the front waist portion 100 comprising the absorbent front panel 230; a rear waist portion 120 with a rear waist edge 122 and left and right rear leg opening edges 124; a crotch portion 130, the crotch portion bridging the front waist portion 100 and the rear waist portion 120; and left and right hip side portions 160 joining the front waist portion to the rear waist portion to form a waist opening with a waist opening edge comprising the front waist edge 102 and the rear waist edge 122, and left and right leg openings; wherein the absorbent front panel 230 extends longitudinally from near the front waist edge 102 or the edge 103*a* of the optional waist band 103 to a minimum rear extent 402 and laterally from a left lateral edge 401*b* to a right lateral edge 401*c*; wherein each of the front waist portion 100, rear waist portion 120 and crotch portion 130 comprises a knitted material; wherein the absorbent front panel 230 comprises an absorbent layer 231*b*, a liquid impermeable barrier layer 231*c* disposed to the outward-facing side of the absorbent layer 231*b*, and no wearer-facing layer 231*a*, preferably wherein the absorbent layer 231*b* is joined to the liquid impermeable barrier layer 231*c* by adhesive, wherein the absorbent front panel 230 is joined to the durable pant by adhesive, tape, thermal bonding, stitching, or a combination thereof, preferably tape, and wherein the durable absorbent pant is washable.

27. The durable absorbent pant of example 26, wherein the liquid impermeable barrier layer 231*c* extends beyond the absorbent layer 231*b*.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A durable absorbent pant comprising a front waist portion, a rear waist portion, a crotch portion bridging the front waist portion and the rear waist portion and comprising an outer body fabric, and left and right hip side portions joining the front waist portion to the rear waist portion to form a waist opening defined by front and rear waist opening edges and a pair of leg openings defined by leg opening edges;

an absorbent panel disposed at least in part in the crotch portion and comprising:

a wearer-facing layer having a first perimeter edge proximate a leg opening of the pair of leg openings;

an absorbent layer; and a barrier layer having a second perimeter edge proximate the leg opening;

an upper tape material having an upper first portion affixed to the wearer-facing layer along the first perimeter edge, and an upper second portion extending laterally outwardly of the first perimeter edge; and a lower tape material having a lower first portion adhered to the barrier layer along the second perimeter edge, and a lower second portion extending laterally outwardly of the second perimeter edge;

the upper second portion and the lower second portion being joined together, and together joined, to the outer body fabric, wherein the wearer-facing layer and the barrier layer are held to each other and/or to the absorbent layer along perimeter edges thereof by a serge stitching, wherein the-serge stitching is covered by one or both the upper tape material and lower tape material, wherein the upper tape material and the lower tape material each comprise an adhesive strip layer and a fabric strip layer, and wherein the upper tape material and the lower tape material are adhered together via the adhesive strip layers thereof.

2. The durable absorbent pant of claim 1 wherein the upper second portion and the lower second portion are joined to the outer body fabric via stitching.

3. The durable absorbent pant of claim 1, wherein the absorbent panel has a handle of about 0.1 gf/mm to about 10 gf/mm.

4. The durable absorbent pant of claim 1, wherein the absorbent panel exhibits a maximum longitudinal elongation of 10 percent to 100 percent.

5. The durable absorbent pant of claim 1, wherein the absorbent panel has a central caliper of less than or equal to about 3.5 mm.

6. The durable absorbent pant of claim 1, wherein the wearer-facing layer comprises a knitted fabric oriented such that a direction of greatest elongation capability is at least approximately parallel with a longitudinal direction of the pant.

7. The durable absorbent pant of claim 1, wherein the wearer-facing layer comprises a rib knit fabric with ribs oriented substantially along a lateral direction of the pant.

8. The durable absorbent pant of claim 1, wherein the absorbent layer comprises terrycloth comprising microfiber yarns, and wherein the microfiber yarns are treated with an antimicrobial agent comprising copper particles.

* * * * *